United States Patent [19]
Lemmon

[11] Patent Number: 5,872,225
[45] Date of Patent: Feb. 16, 1999

[54] METHOD FOR CHARACTERIZING THE NUCLEOTIDE SEQUENCE OF L1CAM AND THE NUCLEOTIDE SEQUENCE CHARACTERIZED THEREBY

[75] Inventor: Vance Lemmon, Shaker Heights, Ohio

[73] Assignee: Case Western Reserve University, Cleveland, Ohio

[21] Appl. No.: 341,843

[22] Filed: Nov. 18, 1994

Related U.S. Application Data

[63] Continuation of Ser. No. 904,991, Jun. 26, 1992, abandoned.
[51] Int. Cl.⁶ .................................................. C07K 14/00
[52] U.S. Cl. ........................................ 530/395; 435/320.1
[58] Field of Search ............................. 536/23.1; 935/18, 935/19, 22; 435/69.1, 172.3, 320.1; 530/395

[56] References Cited

PUBLICATIONS

Harper et al. 1991, Journal of Neurochemistry 56(3): 797–804.
Moos et al. 1988. Nature 334:701–703.
Watson et al. Recombinant DNA; A Short Course pp. 76–78, Scientific American Books, New York.
Wallace et al. 1987. Methods in Enzymology 152:432–442.

*Primary Examiner*—James Ketter
*Assistant Examiner*—Irem Yucel
*Attorney, Agent, or Firm*—Fay, Sharpe, Beall, Fagan, Minnich & McKee

[57] ABSTRACT

The present invention is directed to the isolation and purification of an L1-like molecule (i.e. L1CAM) from human brain. It has been found that the isolated L1CAM molecule supports neurite growth in vitro. Applicants have also cloned and sequenced the entire coding region of human L1CAM, and found that it shows a very high degree of homology to mouse L1cam with 92% identity at the amino acid level. This similarity suggest that L1CAM is an important molecule in normal human nervous system development and nerve regeneration. Overall, there is substantially less homology to chick Ng-CAM; they are 40% identical at the amino acid level but many regions are highly conserved. Comparison of the sequences from human, mouse, chick and Drosophila, indicates that the L1 immunoglobulin domain 2 and fibronectin type III domain 2 are strongly conserved and thus are likely functionally important.

3 Claims, 6 Drawing Sheets

```
Ig 1    17 Mouse L1  ------------------------------------R-R-Q-E-----I------V-HEA-Y------------Y--------Q-V
        17 Human L1  VITEQSPRRLVVFPTDDISLKCEASGKPEVQFRWTRDGVHFKPKEELGVTVYQSPHSGSFTITGNNSNFAQRFQGIYRCFASNKLGTAMSHEIRLM
        17 Ng-CAM    EL--EP-EQ------S---V---V-T-N-P---Y---S-EISPSS-RSTG-      RW-PDRHLVI-ATLA-Q-L--RF----T-A----V-P-ANVI Ig 2   112 Mouse L1  ----------------------------------------------A-P----------FD------S------D------------N--------------P------
       113 Human L1  AEGAPKWPKETVKPVEVEEGESVLPCNPPSAEPLRIYWMNSKILHIKQDERVTMGQNGNLYFANVLTSDNHSDYICHAHFPGTRTIIQKEPIDLRVKATNSMID
       107 Ng-CAM    --NT-Q--KK-T------DP----E-V-PK--L--D-V--A-----S-----D-----S-AMVG-S-P--------L-P---------L----APS-AVRS Ig 3   218 Mouse L1  ------------------------R------S-I-----------H-D---T----I--------N--------T------------------
       219 Human L1  RKPRLLFPTNSSSHLVALQGGPLVLECIAEGFPTPTIKWLRPSGPMPADRVTYQNHNKTIQLLKVGEEDDGEYRCLAENSLGSARHAYYVTEAAP
       213 Ng-CAM    ---------L-RDPQTTTI--R-GSV--------L---WVR-R-LN--LLPGG------F---R-WG-T-S----E-V--GR-T--GTHS------

Ig 4   314 Mouse L1  --Q--------------------------I------MSM-TVN--------------EQ-S--------T------Q-------------
       315 Human L1  YWLHKQSHLYGPGETARLDCQVQGRPQPEVTWRINGIPVEELAKDQKYRIQRGALILSNVQPSDTMVTQCEARNRHGLLLANAYIYVQLP
       307 Ng-CAM    --RR---GVF-----------E-G-K-R-QIQ-S---V-I- A-GAERRWLRG---V-PELR-N-SA-L--------P------FLH-E---

Ig 5   406 Mouse L1  -R--K-----E---------------------------------------S-----------Q--------I-L---Q-E--
       407 Human L1  AKILTADNQTYMAVQGSTAYLLCKAFGAPVPSVQWLDEDGTTVLQDERFFPYANGTLGIRDLQANDTGRYFCLAANDQNNVTIMANLKVKDAT
       398 Ng-CAM    LRM-----E-R-EV-ENQTVF-H-RT------A-N-E--TPTLEPA---D-S-VFT--S-RVSAVRGG-G-V-T-M-Q-AHS-GSLT-L-E-RAP- Ig 6   499 Mouse L1  -------A------------A----------A--------------R---------K--Q------------E-------------------------------
       500 Human L1  QITQGPRSTIEKKGSRVTFTCQASFDPSLQPSIT  WRGDGRDLQELGSDKYFIEDGRLVIHSLDYSDQGNYSCVASTELDVVESRAQLLVVGSPGP
       491 Ng-CAM    R-SAP---ATA---ET---H-G-T---AVT-GELR-LRG-QP-P    -DPR-SVAAEMT-S NV--G-E-TIQ-R---P--SA-AE---R---R--

Fn 1   595 Mouse L1  --H-E---R---K----HL-------------------S----------------------------------S----------
       596 Human L1  VPRLVLSDLHLLTQSQVRVSWSPAEDHNAPIEKYDIEFEDKEMAPEKWYSLGKVPGNQTSTTLKLSPYVHYTFRVTAINKYGPGEPSPVSETVTPEAAPE
       583 Ng-CAM    SRD-   QVMEVDEHR--L--T-GD---S----FVV-E-EEREDLQRGFGAAD---QPWTPP-P---GRFP----V-V--A--R--HHAP-APIE--P----

Fn 2   696 Mouse L1  -----R-------N----------------I--------KQE      T-RK-T------------N-----------------
       697 Human L1  KNPVDVKGEGNETNMVITWKPLRWMDWNAPQVQYRVQWRPQGTRG       PWQEQIVSDPFLVVSNTSTFVPYEIKVQAVNSQGKGPEPQVTIGYSGEDY
       681 Ng-CAM    R--GG--H------G-L----K---PQA----WAR-------LEEP--GGGPSGGF--A--ST-DA-PV---GGLPP-S-PQ-R-----GA---ATPGV-H----L Fn 3   792 Mouse L1  --VS----D-T-F---T---R-----------------WK-------------S-I------------A--------V------L----W-------
       793 Human L1  PQAIPELEGIEILNSSAVLVKWR PVDLAQVKGHLRGYNVTYWREGSQRKHSKRHIHKDHVVVPANTTSVILSGLRPYSSYHLEVQAFNGRGSGPASEFT
       785 Ng-CAM    -LVY--NV-V--L----T-R-TLGGGPKELR--R----FR-L---L-WVGER--R-QAPP-PPQI-QSPA     EDP-FPPVA-T-GG DA--ALLGGLRPWSRYQLRVLVFNGRGDGPPSEPIA-E----

Fn 4   898 Mouse L1  -----------D------H----------L-----VEGES-E--F---S--------L-----N-N-DLQ------QQG--------
       899 Human L1  PGHPEALHLECQSNTSLLLRWQPPLSHNGVLTGYVLSYHPLDEGGKGQLSFNLRDPELRTHNLTDLSPHLRYRFQLQATT KEGPGEAIVREGGTMAL
       911 Ng-CAM    --P--E-RV-RLDD-A-SVERRTFKRSI     -----R-QQVEP-SALPGGSV-----  QCD--RG-NARS----LA-PS  -PR-R-ALQT-GSTKPEPPSPLWSR Fn 5   996 Mouse L1  F-KP----------------------------------------P-G-VSPDHQPQ---------------N-------I--KVLL-HLD-------P--VS
       996 Human L1  SGISDFGNISATAGENYSVVSW VPKEGQCNFREFHILFKALGEEKGGASLS  PQYVSYNQSSYTQWDLQPDTDYEIHLFKERMFRHQMAVKTNGTGRVRLP
      1009 Ng-CAM    F-VGGR-GFHGA-V-FGAAQEDD-EF-V-FMNKSTDEPWRTSGRANS --RRYYLEGLRPGTA-RVQFVGRNRSG-NVA-W-SE       -Q----   -Q
```

FIGURE 4A

Transmembrane

```
1097 Mouse L1    TT-S--S-----A---------I------
1095 Human L1    PAG FATEGWFIGFVSAIILLLVLLILCFI
1102 Ng-CAM      -G-GVC-K------SVV----I-------
```

Cytoplasmic

```
1097 Mouse L1    ---------------------------------------------------------------------  PLGSDDSLADYGGSVDVQFNEDGSFIGQYSGKKEKEAAGNDSSGATSPINPAVALE
1095 Human L1    KRSKGGKYSVKDKEDTQVDSEARPMKDETFGEYRSLESDNEEK AFGSSQPSLNGDIK
1102 Ng-CAM      ------------------EA-KGS-S--GAG-GV-SPGRGPCAA--E---G-----G-------------R-PGAGPGSS-PA-SG-GP-LD
```

FIGURE 4B

METHOD FOR CHARACTERIZING THE NUCLEOTIDE SEQUENCE OF L1CAM AND THE NUCLEOTIDE SEQUENCE CHARACTERIZED THEREBY

This is a continuation of application Ser. No. 07/904,991 filed on Jun. 26, 1992 abandoned.

FIELD OF THE INVENTION

The present invention is directed to the isolation and characterization of the entire coding sequence of human L1 cell adhesion molecule (L1CAM). The invention also relates to the nucleotide sequence (SEQ ID NO: 1) characterized by the present invention and the use of this sequence for studying the role of human L1 cell adhesion molecule (L1CAM) in normal and damaged neuronal tissue. In addition, the invention is directed to the isolated and purified polypeptide chain encoded by the nucleotide sequence of the invention.

BACKGROUND OF THE INVENTION

Cell adhesion molecules (abbreviated CAMs) are neuronal cell surface glycoproteins which help to mediate the cohesive interactions between developing or regenerating neurities. It is believed that proper adhesion of neuronal cells to each other and to their surrounding extracellular matrix is essential for maintaining and/or promoting growth of the neuronal cells.

A number of cell adhesion molecules have been isolated and identified, including neural cell adhesion molecule (N-CAM), nerve growth factor-inducible large external glycoprotein (NILE), neuron-glial CAM (Ng-CAM) and closely related proteins L1 (L1 antigen). These integral membrane glycoproteins, or molecules closely related thereto, have been described by Applicants and others in the nervous system of several species.

Representative examples of such identification and description include L1cam in mouse, (Rathjen, F. G., Schachner, M., Immunocytological And Biochemical Characterization Of A New Neuronal Cell Surface Component (L1 Antigen) Which Is Involved In Cell Adhesion. *EMBO J.* 3:1-10 (1984)); NILE in rat, (McGuire, J. C., Greene, L. A., Furano, A. V., Nerve Growth Factor Stimulates Incorporation Of Fucose Or Glucosamine Into An External Glycoprotein In Cultures Rat PC12 Pheochromocytoma Cells. *Cell* 15:357–365 (1978)); Ng-CAM/8D9/G4 in chick, (Grumet, M., Edelman, G. M., Neuron-Glia Cell Adhesion Molecule Interacts with Neurons and Astroglia via Different Binding Mechanisms. *J. Cell Biol.* 106:487–503 (1988); and, Lemmon, V., McLoon, S., The Appearance Of An L1-Like Molecule In The Chick Primary Visual Pathway, *J. Neurosci.* 6:2987–2994, (1986)); and Neuroglian in Drosophila (Bieber, A. J., Snow, P. M., Hortsch, M., Patel, N. H., Jacobs, J. R., Traquina, Z. R., Schilling, J., Goodman, C. S., Drosophila Neuroglian: A Member Of The Immunoglobulin Superfamily With Extensive Homology To The Vertebrate Neural Adhesion Molecule L1. *Cell* 59:447–460 (1989)).

These molecules share similar biochemical properties, immunological crossreactivity, localization predominantly on axons of projection neurons, homology in nucleotide sequence as well as functional similarity.

The L1 cell adhesion molecule, which was first isolated and characterized in mouse (i.e. L1cam) is a membrane-spanning glycoprotein that has sequence similarity with both fibronectin and the immunoglobulin superfamily. Specifically, L1 cell adhesion molecules possessing six extracellular Ig-like domains, three to five fibronectin (Fn) type III-like repeats, a transmembrane segment, and a small cytoplasmic region. The membrane-spanning region links the extensive extracellular domain to the substantial cytoplasmic domain.

Several lines of evidence suggest that the L1 cell adhesion molecule plays an important role in neuronal growth and fasciculation. First, it is expressed by subpopulations of neurons in the central nervous system and on nerons and Schwann cells in the peripheral nervous system. This expression is early on in developing (Martini, R., Schachner, M., Immunoelectron Microscopic Localization Of Neural Cell Adhesion Molecules (L1, N-CAM, MAG) And Their Shared Carbohydrate Epitope And Myelin Basic Protein (MBP) In Developing Sciatic Nerve. *J. Cell Biol.* 103:2439–2448 (1986)) and regenerating axons (Daniloff, J. K., Chuong, C.-M., Levi, G., Edelman, G. M., Differential Distribution Of Cell Adhesion Molecules During Histogenesis Of The Chick Nervous System. *J. Neurosci.* 6:739–758 (1986); and, Martini, R., Schachner, M., Immunoelectron microscopic localization of neural cell adhesion molecules (L1, N-CAM, MAG) and their shared carbohydrate epitope and myelin basic protein (MBP) in developing sciatic nerve. *J. Cell Biol.* 103:2439–2448 (1986)).

Secondly, since antibodies to L1 disrupt fascicle formation in vitro (Stallcup, W. B., Beasley, L., Involvement Of The Nerve Growth Factor-Inducible Large External Glycoprotein (NILE) In Neurite Fasciculation In Primary Cultures Of Rat Brain. *Proc. Natl. Acad. Sci.* USA 82:1276–1280 (1985)) and in vivo (Landmesser, L., Dahm, L., Schultz, K., Rutishauser, U., Distinct Roles For Adhesion Molecules During Innervation Of Embryonic Chick Muscle. *Dev. Biol.* 130:645–670 (1988)), L1 participates in axonal fasciculate formation.

Finally, it has been shown by Applicants and others that purified L1 is a potent substrate for neurite growth and development (Lagenaur, C., Lemmon, V., A L1-Like Molecule, The 8D9 Antigen, Is A Potent Substrate For Neurite Extension. *Proc. Natl. Acad. Sci.* USA 84:7753–7757 (1987)).

Moreover, a number of observations are consistent with the existence of a L1 human homologue. Human tumors, especially neuroblastoma, demonstrate immunoreactivity to L1 antibodies (Mujoo, K., Spiro, R. C., Reisfeld, R. A., Characterization Of A Unique Glycoprotein Antigen Expressed On The Surface Of Human Neuroblastoma Cells. *J Biol. Chem.* 261:10299–10305 (1986); and, Figarella-Branger, D. F., Durbec, P. L., Rougon, G. N., Differential Spectrum Of Expression Of Neural Cell Adhesion Molecule Isoforms And L1 Adhesion Molecules On Human Neuroectodermal Tumors. *Cancer Research* 50:6364–6370 (1990) ). In addition, Biochemical analysis of a glycoprotein isolated from human brain using an anti-neuroblastoma monoclonal antibody revealed that the antigen was very similar to mouse L1cam, Wolff, J. M., Frank, R., Mujoo, K., Spiro, R. C., Reisfeld, R. A., Rathjen, F. G., A human Brain Glycoprotein Related To The Mouse Cell Adhesion Molecule L1. *J. Biol Chem.* 263:11943–11947 (1988)). To conform with the HGMW approved nomenclative, (Human Gene Mapping Workshop, published 1987 in Cytogenet. Cell Genet., Vol. 46, pages 11–28) mouse L1 cell adhesion molecule is referred hereinafter as L1cam and human L1 cell adhesion molecule is referred to as L1CAM.

Recently, partial sequences obtained for a human genomic clone, Djabali, M., Mattei, M. G., Nguyen, C., Roux, D., Demengeot, J., Denizot, F., Moos, M., Schachner, M., Goridis, C., Jordan, B. R., The Gene Encoding L1, A Neural Adhesion Molecule Of The Immunoglobulin Family, Is Located On The X-Chromosome In Mouse And Man, *Genomics* 7:587–593 (1990) and a human melanoma cDNA clone (Harper, J. R., Prince, J. T., Healy, P. A., Stuart, J. K., Nauman, S. J., Stallcup, W. B., Isolation And Sequence Of Partial cDNA Clones of Human-L1—Homology Of Human And Rodent-L1 In The Cytoplasmic Region, *J. Neurochem.* 56:797–804 (1991) confirmed that a human L1-like molecule exists.

Further studies localized the gene for human L1 to the q28 band on the X chromosome (Djabali, M., Mattei, M. G., Nguyen, C., Roux, D., Demengeot, J., Denizot, F., Moos, M., Schachner, M., Goridis, C., Jordan, B. R., The Gene Encoding L1, A Neural Adhesion Molecule Of The Immunoglobulin Family, Is Located on the X-Chromosome in Mouse and Man, *Genomics* 7:587–593 (1990), the homologous region to the A6-B region of the mouse X chromosome where the L1cam gene is located.

The knowledge that a L1-like molecule exists in humans leads to the conclusion that L1CAM may be important in promoting axon regeneration in trauma or disease states of the human nervous system. Therefore, the Applicants have isolated and purified L1 from human brain and conducted in vitro experiments on the natural substance that demonstrate that human L1CAM, like chick and mouse L1cam, can support neuron attachment and neurite growth.

In addition, Applicants have cloned and sequenced cDNAs encompassing the entire coding region of L1CAM. This information will allow future studies on the structure and function of L1CAM and permit the construction of cell lines expressing L1CAM for in vitro and in vivo experiments on nerve growth and regeneration.

These and other objects and features of the invention will be apparent from the following description and from the claims.

SUMMARY OF THE INVENTION

In one aspect, the present invention is directed to the isolation and purification of an L1-like molecule (i.e. L1CAM) from human brain. It has been found that the isolated L1CAM molecule supports neurite growth in vitro. Applicants have also cloned and sequenced the entire coding region of human L1CAM (SEQ ID NO: 1), and found that it shows a very high degree of homology to mouse L1cam with 92% identity at the amino acid level. This similarity suggest that L1CAM is an important molecule in normal human nervous system development and nerve regeneration. Overall, there is substantially less homology to chick Ng-CAM; they are 40% identical at the amino acid level but many regions are highly conserved. Comparison of the sequences from human, mouse, chick and Drosophila, indicates that the L1 immunoglobulin domain 2 and fibronectin type III domain 2 are strongly conserved and thus are likely functionally important.

In another aspect, present invention provides for a method for isolating and completely characterizing the coding sequence of human L1CAM (SEQ ID NO: 1). Moreover, the invention provides various methods for using the identified nucleotide sequence (or DNA fragments thereof) for evaluating the function of human L1CAM in normal and damaged tissue.

In an additional aspect, the invention relates to procedures for determining and/or correcting genetic or acquired disorders of the central nervous system axonal tract.

Furthermore, the invention provides for use of the sequence information characterized to synthesize the L1CAM glycoprotein itself or fragments thereof. Along this line, the invention relates to use of the identified nucleotide sequence (or DNA parts thereof) to synthesize L1CAM or modifications of this glycoprotein into microorganisms or other hosts which use the gene to synthesize the glycoprotein.

In a further aspect, the present invention provides for use of the cDNAs for comparison of recombinant L1CAM with product purified from human brain. This permits functional studies on the recombinant molecule to be conducted. Similarly, use of the characterized cDNAs, permits the construction of cell lines expressing normal and altered L1CAM for use in transplantation and regeneration studies.

In still another aspect, the invention provides for recombinant DNA cloning vectors and transformed hosts which contain a vector which has a cDNA insert which codes for L1CAM.

BRIEF DESCRIPTION OF THE DRAWINGS

The following is a brief description of the drawings which are presented for the purpose of illustrating the invention and not for the purpose of limiting same.

FIGS. 3A and 3B shows the nucleotide (bottom line) and deduced amino acid (top line) sequence of the coding portion of L1CAM (SEQ ID NO: 1). Untranslated nucleotides are not shown. The boxed nucleotides represent areas of discrepancy as compared with other published L1CAM sequence data. Underlined regions represent the oligonucleotides used for screening the library. The asterisk represents a stop codon. The nucleotide sequence for L1CAM is available through GenBank Data Libraries under Accession No. M64296.

FIGS. 4A and 4B shows a comparison at an amino acid level of L1CAM domains with corresponding domains in L1cam and chick Ng-CAM. Gaps were introduced to maximize identities between the sequences. Identical residues are represented by a hash mark. The amino acids shown as being the transmembrane region include the link between the Fn-5 domain and the presumed membrane spanning region that begins with GWFI. The amino acids shown in FIGS. 4A and 4B correspond to the amino acid sequences, SEQ ID. NOS. 4–39, set forth in the Sequence Listing.

DETAILED DESCRIPTION OF THE INVENTION

L1CAM Purification

L1CAM was isolated and purified by immunoaffinity chromatography using similar purification methods previously described by the Applicants (Lemmon, V., Farr, K., Lagenaur, L1 Mediated Axon Outgrowth Occurs Via A Homophilic Binding Mechanism. *Neuron* 2:1597–1603 (1989)). Briefly, neural membranes from 12 day full term neonatal human brain (the infant succumbed from complications of Trisomy 18) were isolated on sucrose gradients and then extracted with 1% deoxycholate. The extract was then run over a 74-5H7 IgG monoclonal antibody to L1cam affinity column (Lemmon, V., Farr, K., Lagenaur, C., L1 Mediated Axon Outgrowth Occurs Via A Homophilic Binding Mechanism. *Neuron* 2:1597–1603 (1989)). Antigens were eluted with 0.1 M diethylamine (pH 11.5) and the solution rapidly neutralized with Tris-HCl. Fractions were then dialyzed against PBS overnight. Gel electrophoresis of the purified product was performed on a 5% SDS-polyacrylamide gel.

Figure 1:
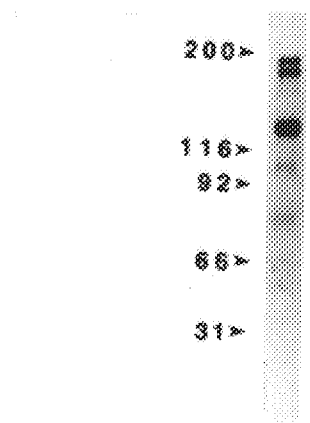
FIG. 1 is a photograph of a silver stained SDS-PAGE gel of immunopurified L1CAM. The molecular weight standards are indicated at the left.

A silver stained SDS-polyacrylamide gel of purified L1CAM is shown in FIG. 1. Notable is the characteristic doublet of bands at 190–180 kDa, a major band at 130 kDa, and minor bands at 105 kDa, 80 kDa, and 62 kDa. This is similar to the pattern reported by others for L1CAM (Mujoo, K., Spiro, R. C., Reisfeld, R. A., Characterization Of A Unique Glycoprotein Antigen Expressed On The Surface Of Human Neuroblastoma Cells. *J Biol. Chem.* 261:10299–10305 (1986); and, Wolff, J. M., Frank, R., Mujoo, K., Spiro, R. C., Reisfeld, R. A., Rathjen, F. G., A Human Brain Glycoprotein Related To The Mouse Cell Adhesion Molecule L1. *J Biol Chem.* 263:11943–11947 (1988)), chick Ng-CAM (Burgoon, M. P., Grumet, M., Mauro, V., Edelman, G. M., Cunningham, B. A., Structure Of The Chicken Neuron-Glial Cell Adhesion Molecule, Ng-CAM: Origin Of The Polypeptides And Relation To The Ig Superfamily. *J. Cell Biol.* 112:1017–1029 (1991) and L1cam (Sadoul, K., Sadoul, R., Faissner, A., Schachner, M., Biochemical Characterization Of Different Molecular Forms Of The Neural Cell Adhesion Molecule L1. *J. Neurochem* 50:510–521 (1988).

Cell Culture

Functional assays of the L1CAM purified from human brain were performed by two neuronal culture methods. Dissociated P1 rat cerebellar cells were plated on L1CAM-nitrocellulose coated plates as previously described by Applicant (Lemmon, V., Farr, K., Lagenaur, C., L1 Mediated Axon Outgrowth Occurs Via A Homophilic Binding Mechanism. *Neuron* 2:1597–1603 (1989). E7 chick retinal strips were grown on L1CAM-nitrocellulose coated plates based on a system developed by Halfter et al. (Halfter, W., Claviez, M., Schwarz, U., Preferential Adhesion Of Tectal Membranes To Anterior Embryonic Chick Retina Neurites. *Nature* 292:67–70 (1981)). Plain nitrocellulose coated with bovine serum albumin was used as a negative control substrate.

Figure 2:
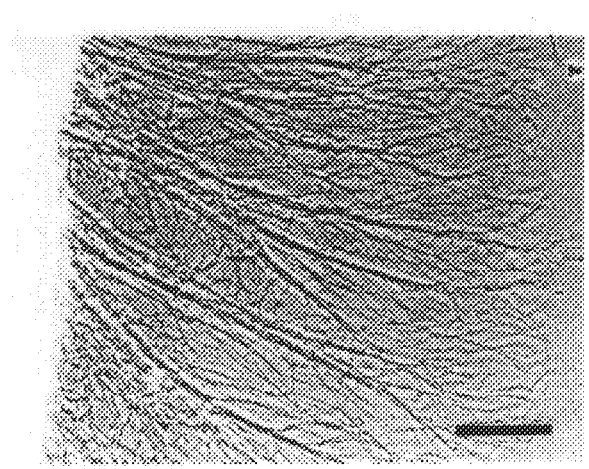
FIG. 2 is a microphotograph of E7 chick retinal explants grown on L1CAM coated dishes. Control dishes coated with BSA had no neurite outgrowth. Scale, bar=100 microns.

As shown in FIG. 2, purified L1CAM was extremely potent in supporting neurite outgrowth. Chick retinal explants produced extended defasciculated neurites on L1CAM (FIG. 2) and dissociated rat cerebellar neurons grew long neurites. Controls grown on nitrocellulose without L1CAM showed poor attachment and no neurite extension.

Molecular Cloning

A human fetal brain cDNA library in Lambda ZAP® II (Stratagene, La Jolla, Calif.) was amplified in the *E. coli* strain XL1-Blue (Stratagene, La Jolla, Calif.). The library was probed with a $^{32}$P 5' end labelled synthetic degenerate oligonucleotides, 50 nucleotides in length (i.e. GAGGA-CACCCAGGTGGACTCTGAGGCCCGACCGA TGAAAGATGAGACCTT) (SEQ ID NO: 2), corresponding to a region that is highly conserved between L1cam and the rat homologue NILE glycoprotein (Prince, J. T., Milona, N., Stallcup, W. B., Characterization Of A Partial cDNA Clone For The NILE Glycoprotein And Identification Of The Encoded Polypeptide Domain. *J. Neurosci* 9:1825–1834 (1989)). The screening was carried out overnight at 30° C. in a solution containing 6xSSC, 5xDenhardts, 0.5% SDS (sodium dodecyl sulfate), 20% formamide and 100 ug/ml salmon sperm DNA.

Figure 5:
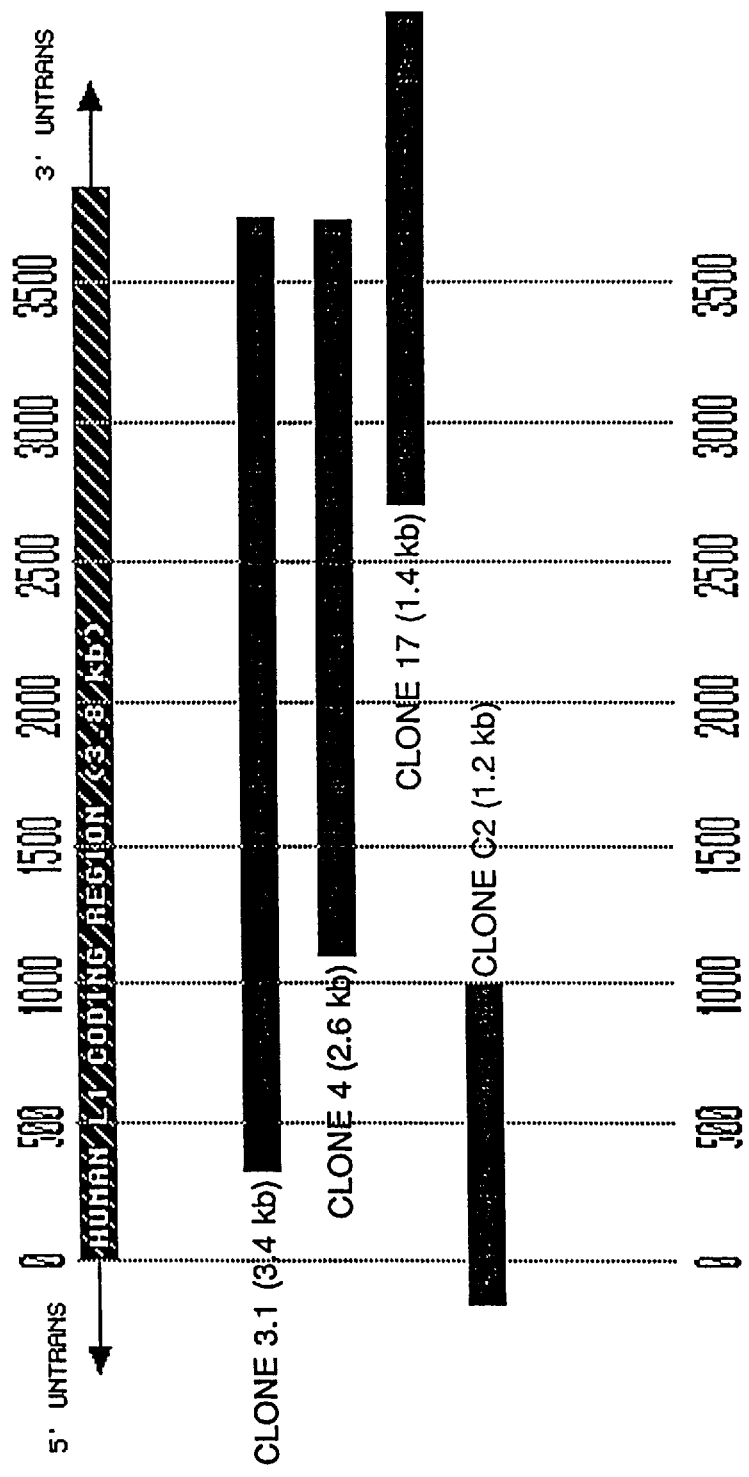
FIG. 5 is a map of the four cloned cDNAs (i.e. 3.1, 4, 17 and C2) that code for parts of L1CAM. A scale demonstrating the size differences in base pairs is shown beside the cloned cDNAs.

A total of $3 \times 10^6$ placques were screened, representing a three-fold screening of the library. Twenty placques were initially positive, however only three of the clones initially isolated from the cDNA library remained positive after successive rounds of screening and proved subsequently to correspond to L1CAM cDNA. After excision of the inserts from the phage vector, these clones were 3.4, 2.6, and 1.4 kb in length and were designated 3.1, 4 and 17 respectively. See FIG. 5. Because none of these contained a start methionine and initial signal sequence, a second screening of the library was performed using a 40 base oligonucleotide (i.e. TGC-CACGCCCACTTCCCAGGCACCAGGACCATCAT TCAGA) (SEQ ID NO: 3) deduced from sequencing the 5' end of clone 3.1. A positive clone from this screening, C2, contained an initiation codon preceded by a stop codon and followed by sequence that corresponded to a hydrophobic stretch of amino acids that is presumed to be a signal sequence, as well as sequence that overlapped with the previously obtained clones. This clone was 1.2 kb in length.

DNA Sequencing

Double stranded DNA sequencing was carried out by the dideoxynucleotide method (Sanger, F. S., Nicklen, S., Coulson, A. R., DNA Sequencing With Chain Terminating Inhibitors. *Proc. Natl. Acad. Sci.* USA 74:5463–5467 (1977)) using a Sequenase Kit (USBC, Cleveland, Ohio) and $^{35}$S-deoxyadenosine 5'-(thio)triphosphate from Amersham, Arlington Heights, Ill. The primers for the reactions were custom synthesized. Sequencing primers to the T7 and T3 promoters were used for the initial sequencing, and subsequent sequencing was done using additional synthetic oligonucleotide primers generated from the newly acquired newly acquired L1CAM sequence. The complete sequence was obtained from both DNA strands. Sequence analysis was carried out using the MacVector® (IBI) sequence analysis program.

Figure 3A:
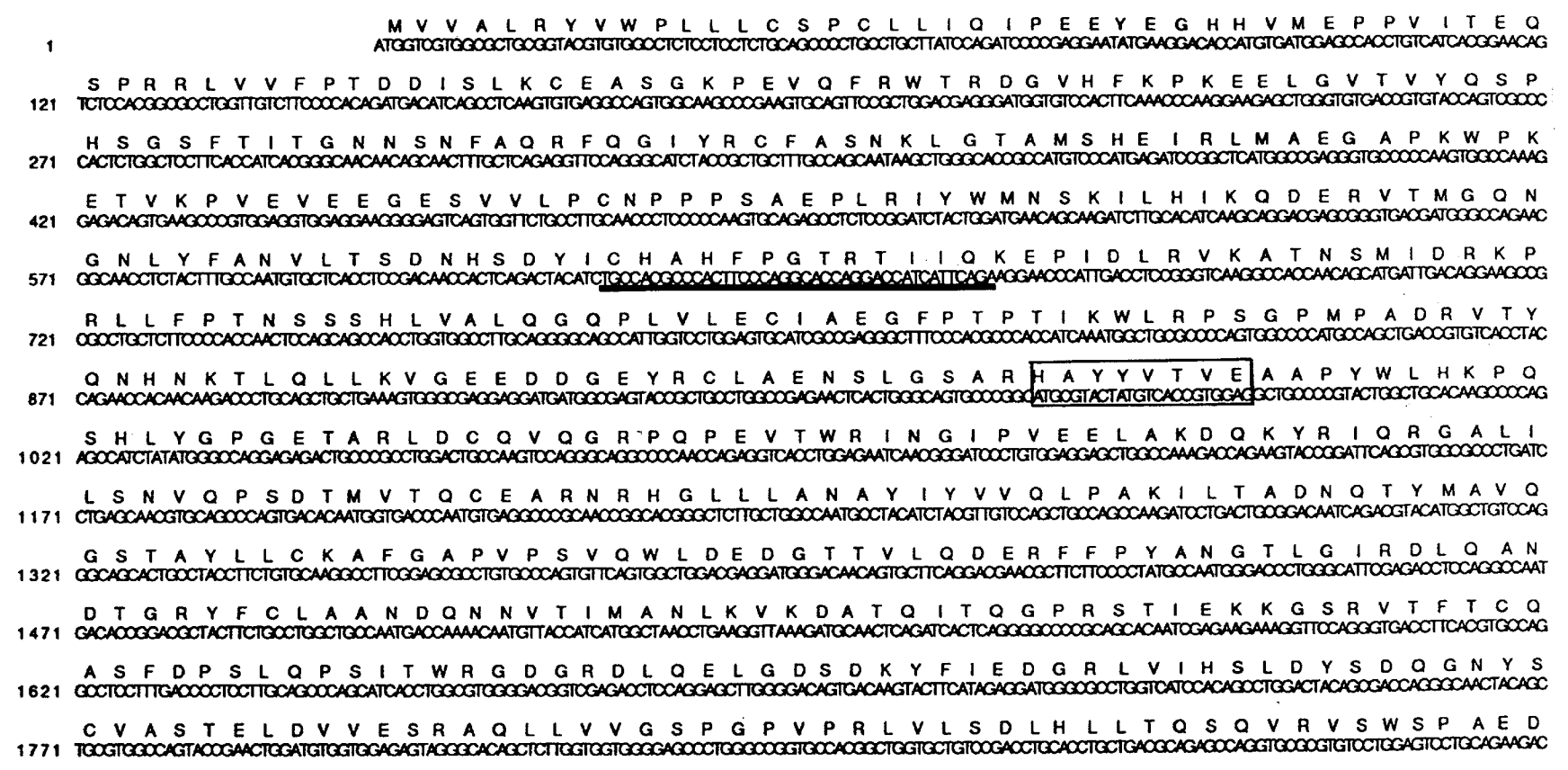
Figure 3B:
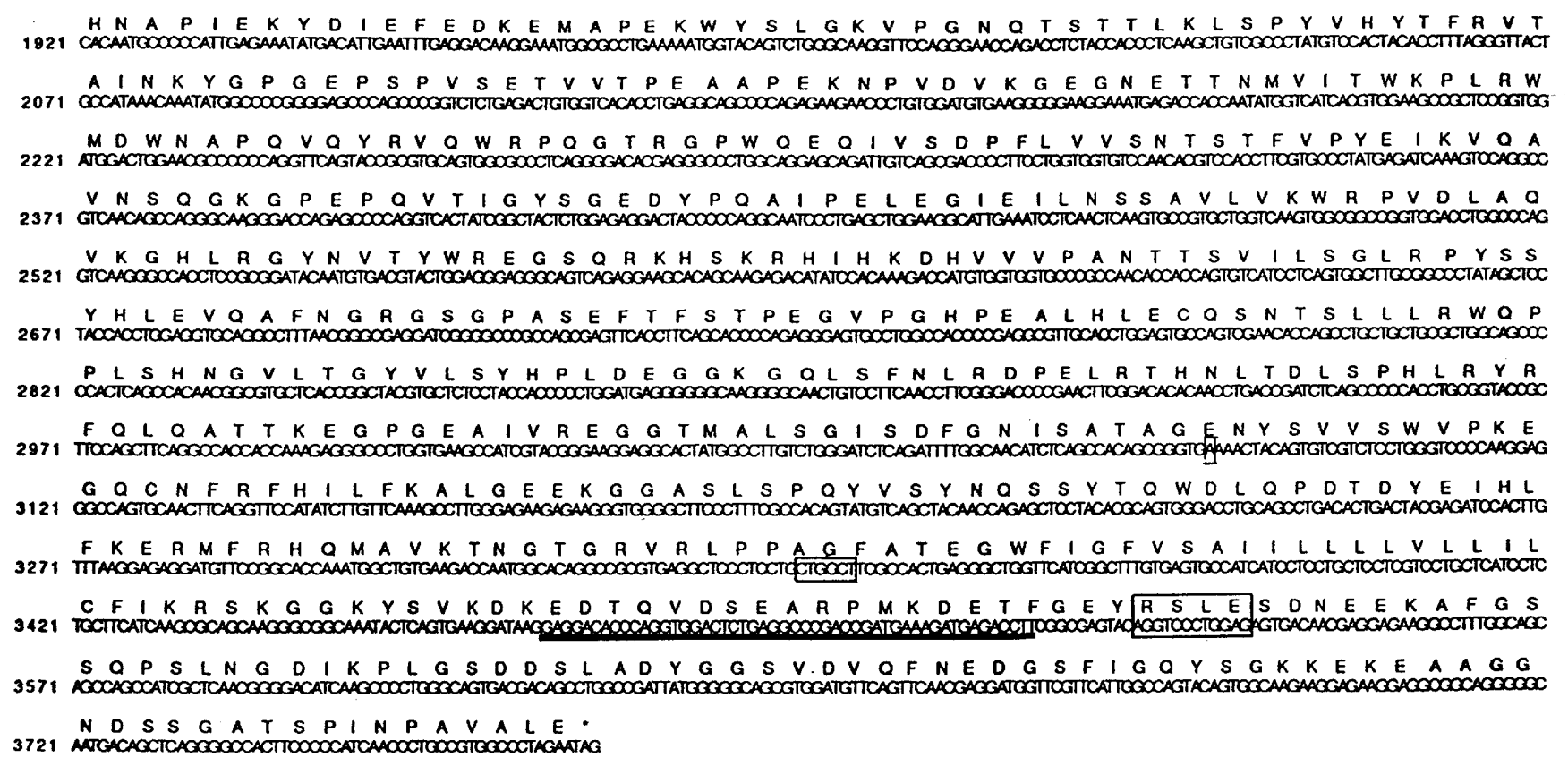

The nucleotide (lower line) and deduced amino acid (upper line) sequence for the L1CAM cDNA coding region is shown in FIGS. 3A and 3B. The open reading frame encodes a protein of 1,256 amino acids and 142,698 Dalton molecular weight. The nucleotide sequence for L1CAM (SEQ ID NO: 1) has been deposited with EMBL/GenBank Data Libraries under Accession No. M64296.

The nucleotide sequences of the human L1CAM and mouse L1cam cDNAs were compared and found to be 85% identical. At the amino acid level, this rose to 92% overall identity (FIGS. 4A amd 4B).

Structurally, L1-related molecules are similar to other immunoglobulin superfamily cell adhesion molecules having a motif of repeating immunoglobulin domains followed by fibronectin type III domains. The L1-like molecules in particular have 6 repeating immunoglobulin C2 (Ig) domains followed by 5 repeating fibronectin type III (Fn) domains (Moos, M., Tacke, R., Scherer, H., Teplow, D., Fruh, K., Schachner, M., Neural Adhesion Molecule L1 As A Member Of The Immunoglobulin Superfamily With Binding Domains Similar To Fibronectin. *Nature* 334:701–703 (1988); and, Burgoon, M. P., Grumet, M., Mauro, V., Edelman, G. M., Cunningham, B. A., Structure Of The Chicken Neuron-Glial Cell Adhesion Molecule, Ng-CAM:

Origin Of The Polypeptides And Relation To The Ig Superfamily. *J. Cell Biol.* 112:1017–1029 (1991)). These are linked to a cytoplasmic portion of the molecule by a transmembrane domain.

A domain by domain comparison of the protein sequence of human L1CAM to mouse L1cam, chick Ng-CAM, and Drosophila neuroglian was performed and is summarized below in Table 1.

Origin Of The Polypeptides And Relation To The Ig Superfamily. *J. Cell Biol.* 112:1017–1029 (1991)). In contrast, mouse NCAM is about 80% identical with chick NCAM and rat fibronectin is about 80% identical with chick fibronectin. They also state that "experiments to identify an L1 homologue in chickens and an Ng-CAM homologue in mice have not yet revealed such molecules".

Despite the poor sequence homology between Ng-CAM and mammalian L1, there are many similarities among the

TABLE 1

Percentage Identity of Amino Acids in Different Domains Compared to Human L1

| Domain | Ig 1 | Ig 2 | Ig 3 | Ig 4 | Ig 5 | Ig 6 | Fn 1 | Fn 2 | Fn 3 | Fn 4 | Fn 5 | TM | CP |
|---|---|---|---|---|---|---|---|---|---|---|---|---|---|
| ML1cam | 83 | 93 | 91 | 87 | 90 | 93 | 89 | 89 | 86 | 82 | 75 | 94 | 100 |
| NGCAM | 44 | 66 | 55 | 57 | 39 | 43 | 38 | 56 | 33 | 30 | 18 | 78 | 63 |
| NGCAM* | 62 | 83 | 71 | 79 | 66 | 56 | 67 | 73 | 58 | 49 | 32 | 100 | 75 |
| Neuroglian | 26 | 32 | 27 | 24 | 29 | 32 | 32 | 36 | 31 | 29 | 18 | 22 | 26 |
| Neuroglian* | 41 | 54 | 47 | 49 | 49 | 48 | 51 | 68 | 50 | 52 | 40 | 67 | 40 |

As indicated above, two short stretches of L1CAM nucleotide sequence have been published previously. A comparison of the genomic sequence obtained by Dijalbi et al. (Djabali, M., Mattei, M. G., Nguyen, C., Roux, D., Demengeot, J., Denizot, F., Moos, M., Schachner, M., Goridis, C., Jordan, B. R., The Gene Encoding L1, A Neural Adhesion Molecule Of The Immunoglobulin Family, Is Located On The X-Chromosome In Mouse And Man. *Genomics* 7:587–593 (1990)) with Applicants is an identical match from nucleotides 991–1091. See FIGS. 3A and 3B. The first 23 nucleotides of the Dijalbi sequence, however, did not match Applicants sequence or the L1cam sequence and likely represents an intron.

The sequence obtained by Harper et al. (Harper, J. R., Prince, J. T., Healy, P. A., Stuart, J. K., Nauman, S. J., Stallcup, W. B., Isolation And Sequence Of Partial cDNA Clones Of Human-L1—Homology Of Human And Rodent-L1 In The Cytoplasmic Region. *J Neurochem* 56:797–804 (1991)) from human melanoma cDNA differs from Applicants at L1CAM nucleotides 3528 to 3540 where Harper et al. show a 12 nucleotide deletion. See FIGS. 3A and 3B. Applicants obtained identical sequence for this region from three independent clones and the sequence matches the corresponding mouse nucleotide sequence perfectly. This discrepancy could represent a mutation in the tumor line or a splicing variant. The sequence also varies between nucleotides 3344–3349 where Harper et al. have an extra 3 nucleotides introduced non-sequentially. Interestingly, Applicants found a one amino acid deletion here as compared to the mouse L1cam sequence with matching of the flanking amino acids on either side. This region was particularly difficult to sequence on the anti-sense strand, requiring dITP reactions to resolve compressions. The coding strand, however, had unambiguous sequence. Applicants found a final difference at base 3086 where Applicants have an A.

A comparison of the sequences of human L1CAM and mouse L1cam with Ng-CAM in FIG. 4 raises a question about the relationship between mammalian L1 and Ng-CAM: are they homologous? Burgoon et al. have suggested that Ng-CAM may not be "equivalent" to L1 due to the relatively low sequence (40%) identity between the two molecules (Burgoon, M. P., Grumet, M., Mauro, V., Edelman, G. M., Cunningham, B. A., Structure Of The Chicken Neuron-Glial Cell Adhesion Molecule, Ng-CAM:

molecules. If conservative amino acid substitutions in Ng-CAM are permitted, the overall similarity between L1CAM and Ng-CAM rises to 66%. The Ig domains show relatively higher degrees of similarity, up to 83%, with 75% conservation of the cytoplasmic domain. Furthermore, the overall structure of the molecule is preserved from species to species; there are 6 Ig domains and 5 Fn domains in each molecule and each structural domain in the chick molecule is most closely related to the same domain in the human. The domains that show the highest degree of similarity between human and mouse (Ig 2, Fn 2, the transmembrane and cytoplasmic domain) also demonstrate the most similarity between human and chick. The relatively variable domains between human L1CAM and mouse L1cam (Ig 1, Fn 4 and Fri 5) also have relatively low homologies between human and chick. This is also true when comparing L1CAM to Drosophila neuroglian.

Immunological and biochemical experiments demonstrate many similarities between mammalian L1 and Ng-CAM. Antibodies against mammalian L1 from different species crossreact with Ng-CAM. Purification of L1 and Ng-CAM from brain produces a similar polypeptide pattern on SDS-PAGE and there is substantial evidence that there are protease sensitive sites at the same two locations in both L1 and Ng-CAM (Sadoul, R., Kirchhoff, F., Schachner, M., A Protein Kinase Activity Is Associated With And Specifically Phosphorylates The Neural Cell Adhesion Molecule L1. *J. Neurochem.* 53:1471–1478 (1988); Prince, J. T., Milona, N., Stallcup, W. B., Characterization Of A Partial cDNA Clone For The NILE Glycoprotein And Identification Of The Encoded Polypeptide Domain. *J. Neurosci.* 9:1825–1834 (1989); and, Burgoon, M. P., Grumet, M., Mauro, V., Edelman, G. M., Cunningham, B. A., Structure Of The Chicken Neuron-Glial Cell Adhesion Molecule, Ng-CAM: Origin Of The Polypeptides And Relation To The Ig Superfamily. *J. Cell Biol.* 112:1017–1029 (1991)). The anatomical distribution of L1, despite minor variations, shows striking similarity between chick and mammals. For example, almost all projection axons in the CNS and PNS express L1 or Ng-CAM in the corresponding species.

Functional experiments have shown that anti-L1 and anti-Ng-CAM antibodies disrupt axon fasciculation in both chicks and mammals (Stallcup, W. B., Beasley, L., Involvement Of The Nerve Growth Factor-Inducible Large External Glycoprotein (NILE) In Neurite Fasciculation In Primary Cultures Of Rat Brain. *Proc. Natl. Acad. Sci.* USA 82:1276–1280 (1985); and, Rathjen, F. G., Schachner, M., Immunocytological And Biochemical Characterization Of A New Neuronal Cell Surface Component (L1 Antigen) Which Is Involved In Cell Adhesion. *EMBO J.* 3:1–10 (1984)) and inhibit neuron-neuron adhesion (Keilhauer, G., Faissner, A., Schachner, M., Differential Inhibition Of Neurone-Neurone, Neurone-Astrocyte and Astrocyte-Astrocyte Adhesion By L1, L2 And N-CAM Antibodies. *Nature* 316:728–730 (1985); Grumet, M., Hoffman, S., Edelman, G. M., Two Antigenically Related Neuronal Cell Adhesion Molecules Of Different Specificities Mediate Neuron-Neuron And Neuron-Glia Adhesion. *Proc. Natl. Acad. Sci.* USA 81:267–271 (1984)). They also perturb migration of granule cells from the external granule cell layer to the internal granule cell layer in the cerebellum (Lindner, J., Rathjen, F. G., Schachner, M., L1 mono- and polyclonal antibodies modify cell migration in early postnatal mouse cerebellum. *Nature* 305:427–430 (1983); and, Hoffman, S., Friedlander, D. R., Chuong, C.-M., Grumet, M., Edelman, G. M., Differential Contributions Of Ng-CAM And N-CAM To Cell Adhesion In Different Neural Regions. *J. Cell Biol.* 103:145–158. (1986)).

Finally, studies with purified L1 and with Ng-CAM show that mammalian cells can bind to chick Ng-CAM and that chick neurons can bind to mammalian L1 in a homophilic binding interaction between the L1cam and the chick Ng-CAM (Lemmon, V., Farr, K., Lagenaur, C., L1 Mediated Axon Outgrowth Occurs Via A Homophilic Binding Mechanism. *Neuron* 2:1597–1603 (1989)). Therefore, while there are clearly structural differences between Ng-CAM and L1 it seems most likely that they represent homologous and not merely analogous molecules.

Comparison of L1CAM, L1cam, rat NILE and chick Ng-CAM confirms previous reports that the cytoplasmic portion of this molecule is very highly conserved, suggesting an important functional role for this region of the molecule (Prince, J. T., Milona, N., Stallcup, W. B., Characterization Of A Partial cDNA Clone For The NILE Glycoprotein And Identification Of The Encoded Polypeptide Domain. *J. Neurosci.* 9:1825–1834 (1989); and, Harper, J. R., Prince, J. T., Healy, P. A., Stuart, J. K., Nauman, S. J., Stallcup, W. B., Isolation And Sequence Of Partial cDNA Clones of Human-L1—Homology Of Human And Rodent-L1 In The Cytoplasmic Region. *J. Neurochem* 56:797–804 (1991)). Evidence points to an interaction of L1 with the cytoskeleton, directly or indirectly, because in differentiated neuroblastomas L1 is relatively immobile (Pollerberg, G. E., Davoust, J., Schachner, M., Lateral Mobility Of The Cell Adhesion Molecule-L1 Within The Surface Membrane Of Morphologically Undifferentiated And Differentiated Neuroblastoma Cells. *European Journal of Neuroscience* 2:712–717 (1990)).

However, on axons and growth cones of chick retinal ganglion cells, L1 is freely diffusible (Drazba, J., Lemmon, V., Cell adhesion molecules 8D9 and NCAM move independently in the plane of axon membranes. *Soc. for Neurosci.*, St. Louis, Mo., (1990)). This suggests that attachment to the cytoskeleton is not a prerequisite for functional binding as is the case for cadherins (Nagafuchi, A., Takeichi, M., Cell binding function of E-cadherin is regulated by the cytoplasmic domain. EMBO J. 7:3679–3684 (1988)).

The cytoplasmic domain of L1 also may be involved in regulating cell adhesion molecule function. L1 is phosphorylated and is associated with a casein kinase (Sadoul, R., Kirchhoff, F., Schachner, M., A Protein Kinase Activity Is Associated With And Specifically Phosphorylates The Neural Cell Adhesion Molecule L1. *J. Neurochem.* 53:1471–1478 (1988)). Anti-L1 antibody binding to L1 on has been shown to alter intracellular calcium and pH (Schuch, U., Lohse, M. J., Schachner, M., Neural Cell Adhesion Molecules Influence Second Messenger Systems. *Neuron* (1989)). Agents such as TPA or okadaic acid that increase cytoplasmic phosphorylation increase fasciculation in a manner consistent with increased affinity of L1 for its ligand (unpublished results; Cervello, Lemmon, Rutishauser). This evidence indicates that L1 either regulates cell function or has its function regulated via its cytoplasmic region.

Interspecies comparison of the amino acid sequence of the extracellular portion of L1 suggests that the Ig domain 2 and Fn domain 2 may have some conserved function since these are the immunoglobulin and fibronectin domains with greatest homology. One possibility is that the Ig domain 2 is important in L1—L1 homophilic binding. The Ig domains 2 and 3 of NCAM are believed to be involved in heparin and cell binding (Frelinger, A. L., Rutishauser, U., Topography of N-CAM Structural And Functional Determinants II. Placement Of Monoclonal Antibody Epitopes. *J. Cell Biol.* 103:1729–1737 (1986); and, Cole, G. J., Akeson, R., Identification If A Heparin Binding Domain Of The Neural Cell Adhesion Molecule N-CAM Using Synthetic Peptides. Neuron 2:1157–1165 (1989)). This demonstrates that Ig superfamily molecules do not necessarily bind amino terminus to amino terminus. It is also possible that a large region of L1 is involved in L1—L1 binding, similar to the manner in which Ig heavy chains bind to each other; according to this model, the L1 Ig domains would bind in a long parallel or anti-parallel interaction.

This possibility is consistent with the report that all monoclonal antibodies to G4 (thought to be identical with chick Ng-CAM) that were tested were able to inhibit G4—G4 binding (Chang, S., Rathjen, F. G., Raper, J. A., Neurite Outgrowth Promoting Activity Of G4 And Its Inhibition By Monoclonal Antibodies. *J Neurosc R* 25:180–186 (1990)). No highly positively charged regions were observed in any of the Ig domains that would be analogous to the heparin binding domain in the second Ig domain of NCAM (Cole, G. J., Akeson, R., Identification Of A Heparin Binding Domain Of The Neural Cell Adhesion Molecule N-CAM Using Synthetic Peptides. *Neuron* 2:1157–1165 (1989)). However, the second Ig domain of L1 and Ng-CAM does have a highly negatively charged region with 4 out of 6 amino acids being aspartic acid or glutamic acid. The third Fn domain of L1 has one region with 9 out of 12 positively charged amino acids. A similar region is present in L1cam but is absent from chick. Conclusions about structure-function relations must await more detailed experiments using well defined antibodies and mutated forms of L1.

The information provided above extends previous work by providing the entire coding sequence of human L1CAM and demonstrating that like the related molecules in mouse, rat and chick, L1CAM purified from human brain can support neurite growth. The structural knowledge gained allows comparisons with nearby and more distant species, mice, chick and Drosophila and speculation about structurally important areas of the molecule. The results of in vitro testing of natural L1CAM support the idea that L1CAM is likely to be an important molecule in the development of the human nervous system by providing evidence that L1CAM can mediate neurite growth. This complements reports that the human L1 gene is on the X chromosome in a region were disease of CNS axonal tract development has been mapped (Djabali et al., 1990), and strengthens the need for further understanding of the molecule. Use of the cDNA will enable comparison of recombinant L1CAM with the product purified from human brain and permit functional studies on the recombinant molecule in vitro. Moreover, using the cDNA, cell lines can be constructed expressing normal and altered L1CAM for use in transplantation or regeneration studies.

Furthermore, as a result of the isolation and complete characterization of the nucleotide sequence, the present invention is also directed to the use of the nucleotide sequence (SEQ ID NO: 1) and/or the cDNA clones thereof, for tests that can be used to determine genetic or acquired disorders of neuronal cells using L1CAM DNA probes specific for the identified nucleotide sequence (or DNA fragments thereof) or antibodies to the products coded by the nucleotide sequence or cDNA. More particularly, such uses include a method for identifying the gene coding for the L1CAM which comprises hybridizing a cDNA which codes for part of the L1CAM with human genomic DNA, and determining whether the cDNA anneals to the genomic DNA.

In addition, the present invention relates to the use of gene fragments generated through amplification from human genomic or cloned DNA for detection and analysis of the gene, such as in the detection of mutations. The gene can be used for the production of L1CAM protein. A method for amplifying a nucleotide sequence specific for the human gene for the L1CAM from biological samples containing human genomic DNA using the synthetic oligonucleotide primers of the present invention which contain either a nucleotide sequence from the gene or from the cDNAs encoding axions of the genes, such a method would comprise the steps of synthesizing the oligonucleotides containing the nucleotide sequence wherein the nucleotide sequence are specific for the gene for the L1CAM, allowing the oligonucleotides to anneal to the specific sequences in the sample containing the human genomic DNA, synthesizing a copy of each strand of the DNA by polymerase chain reaction, and denaturing the sample to separate the DNA strands from each other.

Moreover, as elaborated above, the present invention also relates to the potential use of the nucleotide sequence synthesized above for cloning purposes. Other alterative embodiments for new and unique uses of nucleotide sequences, the CDNA clones, etc. may be utilized by procedures that are well known in the art.

The invention has been described with reference to the preferred embodiments. Obviously, modifications and alterations will occur to others upon reading and understanding the preceding detailed description. It is intended that all such alterations and modifications insofar as they come within the scope of the appended claims or the equivalents thereof.

SEQUENCE LISTING ( 1 ) GENERAL INFORMATION:

( i i i ) NUMBER OF SEQUENCES: 39

( 2 ) INFORMATION FOR SEQ ID NO: 1:

( i ) SEQUENCE CHARACTERISTICS:
        ( A ) LENGTH: 3774
        ( B ) TYPE: nucleic acid
        ( C ) STRANDEDNESS: single
        ( D ) TOPOLOGY: linear ( i i ) MOLECULE TYPE: cDNA ( i i i ) HYPOTHETICAL: irrelevant ( i v ) ANTI-SENSE: no ( v i ) ORIGINAL SOURCE:
        ( A ) ORGANISM: Homo Sapiens
        ( B ) INDIVIDUAL ISOLATE: 17-18 week fetus ( v i i ) IMMEDIATE SOURCE:
        ( A ) LIBRARY: Stratagene cDNA Library 936206
        ( B ) CLONE: synthesis of 4 clones ( x ) PUBLICATION INFORMATION:
        ( A ) AUTHORS: Hlavin, Mary Louise
                Lemmon, Vance
        ( B ) TITLE: Molecular structure and functional
                testing of human L1CAM: an
                interspecies comparison.
        ( C ) JOURNAL: GENOMICS
        ( D ) VOLUME: 11
        ( E ) ISSUE:
        ( F ) PAGES: 416-423
        ( G ) DATE: 1991
        ( K ) RELEVANT RESIDUES IN SEQ ID NO: 1 to 3774

( x i ) SEQUENCE DESCRIPTION: SEQ ID NO: 1:

ATG GTC GTG GCG CTG CGG TAC GTG TGG CCT CTC CTC CTC TGC AGC CCC    4 8

-continued

| | | | | | | | | | | | | | | | | |
|---|---|---|---|---|---|---|---|---|---|---|---|---|---|---|---|---|
| Met | Val | Val | Ala | Leu | Arg | Tyr | Val | Trp | Pro | Leu | Leu | Leu | Cys | Ser | Pro | |
| 1 | | | | 5 | | | | | 10 | | | | | 15 | | |

| TGC | CTG | CTT | ATC | CAG | ATC | CCC | GAG | GAA | TAT | GAA | GGA | CAC | CAT | GTG | ATG | 96 |
|---|---|---|---|---|---|---|---|---|---|---|---|---|---|---|---|---|
| Cys | Leu | Leu | Ile | Gln | Ile | Pro | Glu | Glu | Tyr | Glu | Gly | His | His | Val | Met | |
| | | | 20 | | | | | 25 | | | | | 30 | | | |

| GAG | CCA | CCT | GTC | ATC | ACG | GAA | CAG | TCT | CCA | CGG | CGC | CTG | GTT | GTC | TTC | 144 |
|---|---|---|---|---|---|---|---|---|---|---|---|---|---|---|---|---|
| Glu | Pro | Pro | Val | Ile | Thr | Glu | Gln | Ser | Pro | Arg | Arg | Leu | Val | Val | Phe | |
| | | 35 | | | | | 40 | | | | | 45 | | | | |

| CCC | ACA | GAT | GAC | ATC | AGC | CTC | AAG | TGT | GAG | GCC | AGT | GGC | AAG | CCC | GAA | 192 |
|---|---|---|---|---|---|---|---|---|---|---|---|---|---|---|---|---|
| Pro | Thr | Asp | Asp | Ile | Ser | Leu | Lys | Cys | Glu | Ala | Ser | Gly | Lys | Pro | Glu | |
| 50 | | | | | 55 | | | | | 60 | | | | | | |

| GTG | CAG | TTC | CGC | TGG | ACG | AGG | GAT | GGT | GTC | CAC | TTC | AAA | CCC | AAG | GAA | 240 |
|---|---|---|---|---|---|---|---|---|---|---|---|---|---|---|---|---|
| Val | Gln | Phe | Arg | Trp | Thr | Arg | Asp | Gly | Val | His | Phe | Lys | Pro | Lys | Glu | |
| 65 | | | | | 70 | | | | | 75 | | | | | 80 | |

| GAG | CTG | GGT | GTG | ACC | GTG | TAC | CAG | TCG | CCC | CAC | TCT | GGC | TCC | TTC | ACC | 288 |
|---|---|---|---|---|---|---|---|---|---|---|---|---|---|---|---|---|
| Glu | Leu | Gly | Val | Thr | Val | Tyr | Gln | Ser | Pro | His | Ser | Gly | Ser | Phe | Thr | |
| | | | | 85 | | | | | 90 | | | | | 95 | | |

| ATC | ACG | GGC | AAC | AAC | AGC | AAC | TTT | GCT | CAG | AGG | TTC | CAG | GGC | ATC | TAC | 336 |
|---|---|---|---|---|---|---|---|---|---|---|---|---|---|---|---|---|
| Ile | Thr | Gly | Asn | Asn | Ser | Asn | Phe | Ala | Gln | Arg | Phe | Gln | Gly | Ile | Tyr | |
| | | | 100 | | | | | 105 | | | | | 110 | | | |

| CGC | TGC | TTT | GCC | AGC | AAT | AAG | CTG | GGC | ACC | GCC | ATG | TCC | CAT | GAG | ATC | 384 |
|---|---|---|---|---|---|---|---|---|---|---|---|---|---|---|---|---|
| Arg | Cys | Phe | Ala | Ser | Asn | Lys | Leu | Gly | Thr | Ala | Met | Ser | His | Glu | Ile | |
| | | 115 | | | | | 120 | | | | | 125 | | | | |

| CGG | CTC | ATG | GCC | GAG | GGT | GCC | CCC | AAG | TGG | CCA | AAG | GAG | ACA | GTG | AAG | 432 |
|---|---|---|---|---|---|---|---|---|---|---|---|---|---|---|---|---|
| Arg | Leu | Met | Ala | Glu | Gly | Ala | Pro | Lys | Trp | Pro | Lys | Glu | Thr | Val | Lys | |
| | 130 | | | | | 135 | | | | | 140 | | | | | |

| CCC | GTG | GAG | GTG | GAG | GAA | GGG | GAG | TCA | GTG | GTT | CTG | CCT | TGC | AAC | CCT | 480 |
|---|---|---|---|---|---|---|---|---|---|---|---|---|---|---|---|---|
| Pro | Val | Glu | Val | Glu | Glu | Gly | Glu | Ser | Val | Val | Leu | Pro | Cys | Asn | Pro | |
| 145 | | | | | 150 | | | | | 155 | | | | | 160 | |

| CCC | CCA | AGT | GCA | GAG | CCT | CTC | CGG | ATC | TAC | TGG | ATG | AAC | AGC | AAG | ATC | 528 |
|---|---|---|---|---|---|---|---|---|---|---|---|---|---|---|---|---|
| Pro | Pro | Ser | Ala | Glu | Pro | Leu | Arg | Ile | Tyr | Trp | Met | Asn | Ser | Lys | Ile | |
| | | | 165 | | | | | 170 | | | | | 175 | | | |

| TTG | CAC | ATC | AAG | CAG | GAC | GAG | CGG | GTG | ACG | ATG | GGC | CAG | AAC | GGC | AAC | 576 |
|---|---|---|---|---|---|---|---|---|---|---|---|---|---|---|---|---|
| Leu | His | Ile | Lys | Gln | Asp | Glu | Arg | Val | Thr | Met | Gly | Gln | Asn | Gly | Asn | |
| | | | 180 | | | | | 185 | | | | | 190 | | | |

| CTC | TAC | TTT | GCC | AAT | GTG | CTC | ACC | TCC | GAC | AAC | CAC | TCA | GAC | TAC | ATC | 624 |
|---|---|---|---|---|---|---|---|---|---|---|---|---|---|---|---|---|
| Leu | Tyr | Phe | Ala | Asn | Val | Leu | Thr | Ser | Asp | Asn | His | Ser | Asp | Tyr | Ile | |
| | | 195 | | | | | 200 | | | | | 205 | | | | |

| TGC | CAC | GCC | CAC | TTC | CCA | GGC | ACC | AGG | ACC | ATC | ATT | CAG | AAG | GAA | CCC | 672 |
|---|---|---|---|---|---|---|---|---|---|---|---|---|---|---|---|---|
| Cys | His | Ala | His | Phe | Pro | Gly | Thr | Arg | Thr | Ile | Ile | Gln | Lys | Glu | Pro | |
| | 210 | | | | | 215 | | | | | 220 | | | | | |

| ATT | GAC | CTC | CGG | GTC | AAG | GCC | ACC | AAC | AGC | ATG | ATT | GAC | AGG | AAG | CCG | 720 |
|---|---|---|---|---|---|---|---|---|---|---|---|---|---|---|---|---|
| Ile | Asp | Leu | Arg | Val | Lys | Ala | Thr | Asn | Ser | Met | Ile | Asp | Arg | Lys | Pro | |
| 225 | | | | | 230 | | | | | 235 | | | | | 240 | |

| CGC | CTG | CTC | TTC | CCC | ACC | AAC | TCC | AGC | AGC | CAC | CTG | GTG | GCC | TTG | CAG | 768 |
|---|---|---|---|---|---|---|---|---|---|---|---|---|---|---|---|---|
| Arg | Leu | Leu | Phe | Pro | Thr | Asn | Ser | Ser | Ser | His | Leu | Val | Ala | Leu | Gln | |
| | | | | 245 | | | | | 250 | | | | | 255 | | |

| GGG | CAG | CCA | TTG | GTC | CTG | GAG | TGC | ATC | GCC | GAG | GGC | TTT | CCC | ACG | CCC | 816 |
|---|---|---|---|---|---|---|---|---|---|---|---|---|---|---|---|---|
| Gly | Gln | Pro | Leu | Val | Leu | Glu | Cys | Ile | Ala | Glu | Gly | Phe | Pro | Thr | Pro | |
| | | | 260 | | | | | 265 | | | | | 270 | | | |

| ACC | ATC | AAA | TGG | CTG | CGC | CCC | AGT | GGC | CCC | ATG | CCA | GCT | GAC | CGT | GTC | 864 |
|---|---|---|---|---|---|---|---|---|---|---|---|---|---|---|---|---|
| Thr | Ile | Lys | Trp | Leu | Arg | Pro | Ser | Gly | Pro | Met | Pro | Ala | Asp | Arg | Val | |
| | | 275 | | | | | 280 | | | | | 285 | | | | |

| ACC | TAC | CAG | AAC | CAC | AAC | AAG | ACC | CTG | CAG | CTG | CTG | AAA | GTG | GGC | GAG | 912 |
|---|---|---|---|---|---|---|---|---|---|---|---|---|---|---|---|---|
| Thr | Tyr | Gln | Asn | His | Asn | Lys | Thr | Leu | Gln | Leu | Leu | Lys | Val | Gly | Glu | |
| | 290 | | | | | 295 | | | | | 300 | | | | | |

| GAG | GAT | GAT | GGC | GAG | TAC | CGC | TGC | CTG | GCC | GAG | AAC | TCA | CTG | GGC | AGT | 960 |
|---|---|---|---|---|---|---|---|---|---|---|---|---|---|---|---|---|
| Glu | Asp | Asp | Gly | Glu | Tyr | Arg | Cys | Leu | Ala | Glu | Asn | Ser | Leu | Gly | Ser | |
| 305 | | | | | 310 | | | | | 315 | | | | | 320 | |

| GCC | CGG | CAT | GCG | TAC | TAT | GTC | ACC | GTG | GAG | GCT | GCC | CCG | TAC | TGG | CTG | 1008 |

| | | | | | | | | | | | | | | | |
|---|---|---|---|---|---|---|---|---|---|---|---|---|---|---|---|
| Ala | Arg | His | Ala | Tyr<br>325 | Tyr | Val | Thr | Val<br>330 | Glu | Ala | Ala | Pro | Tyr<br>335 | Trp | Leu |

| CAC | AAG | CCC | CAG | AGC | CAT | CTA | TAT | GGG | CCA | GGA | GAG | ACT | GCC | CGC | CTG | 1056 |
|---|---|---|---|---|---|---|---|---|---|---|---|---|---|---|---|---|
| His | Lys | Pro | Gln<br>340 | Ser | His | Leu | Tyr | Gly<br>345 | Pro | Gly | Glu | Thr | Ala<br>350 | Arg | Leu | |
| GAC | TGC | CAA | GTC | CAG | GGC | AGG | CCC | CAA | CCA | GAG | GTC | ACC | TGG | AGA | ATC | 1104 |
| Asp | Cys | Gln<br>355 | Val | Gln | Gly | Arg | Pro | Gln<br>360 | Pro | Glu | Val | Thr | Trp<br>365 | Arg | Ile | |
| AAC | GGG | ATC | CCT | GTG | GAG | GAG | CTG | GCC | AAA | GAC | CAG | AAG | TAC | CGG | ATT | 1152 |
| Asn | Gly | Ile<br>370 | Pro | Val | Glu | Glu | Leu<br>375 | Ala | Lys | Asp | Gln | Lys<br>380 | Tyr | Arg | Ile | |
| CAG | CGT | GGC | GCC | CTG | ATC | CTG | AGC | AAC | GTG | CAG | CCC | AGT | GAC | ACA | ATG | 1200 |
| Gln<br>385 | Arg | Gly | Ala | Leu | Ile<br>390 | Leu | Ser | Asn | Val | Gln<br>395 | Pro | Ser | Asp | Thr | Met<br>400 | |
| GTG | ACC | CAA | TGT | GAG | GCC | CGC | AAC | CGG | CAC | GGG | CTC | TTG | CTG | GCC | AAT | 1248 |
| Val | Thr | Gln | Cys | Glu<br>405 | Ala | Arg | Asn | Arg | His<br>410 | Gly | Leu | Leu | Leu | Ala<br>415 | Asn | |
| GCC | TAC | ATC | TAC | GTT | GTC | CAG | CTG | CCA | GCC | AAG | ATC | CTG | ACT | GCG | GAC | 1296 |
| Ala | Tyr | Ile | Tyr<br>420 | Val | Val | Gln | Leu | Pro<br>425 | Ala | Lys | Ile | Leu | Thr<br>430 | Ala | Asp | |
| AAT | CAG | ACG | TAC | ATG | GCT | GTC | CAG | GGC | AGC | ACT | GCC | TAC | CTT | CTG | TGC | 1344 |
| Asn | Gln | Thr<br>435 | Tyr | Met | Ala | Val | Gln<br>440 | Gly | Ser | Thr | Ala | Tyr<br>445 | Leu | Leu | Cys | |
| AAG | GCC | TTC | GGA | GCG | CCT | GTG | CCC | AGT | GTT | CAG | TGG | CTG | GAC | GAG | GAT | 1392 |
| Lys | Ala<br>450 | Phe | Gly | Ala | Pro | Val<br>455 | Pro | Ser | Val | Gln | Trp<br>460 | Leu | Asp | Glu | Asp | |
| GGG | ACA | ACA | GTG | CTT | CAG | GAC | GAA | CGC | TTC | TTC | CCC | TAT | GCC | AAT | GGG | 1440 |
| Gly<br>465 | Thr | Thr | Val | Leu | Gln<br>470 | Asp | Glu | Arg | Phe | Phe<br>475 | Pro | Tyr | Ala | Asn | Gly<br>480 | |
| ACC | CTG | GGC | ATT | CGA | GAC | CTC | CAG | GCC | AAT | GAC | ACC | GGA | CGC | TAC | TTC | 1488 |
| Thr | Leu | Gly | Ile | Arg<br>485 | Asp | Leu | Gln | Ala | Asn<br>490 | Asp | Thr | Gly | Arg | Tyr<br>495 | Phe | |
| TGC | CTG | GCT | GCC | AAT | GAC | CAA | AAC | AAT | GTT | ACC | ATC | ATG | GCT | AAC | CTG | 1536 |
| Cys | Leu | Ala | Ala<br>500 | Asn | Asp | Gln | Asn | Asn<br>505 | Val | Thr | Ile | Met | Ala<br>510 | Asn | Leu | |
| AAG | GTT | AAA | GAT | GCA | ACT | CAG | ATC | ACT | CAG | GGG | CCC | CGC | AGC | ACA | ATC | 1584 |
| Lys | Val | Lys | Asp<br>515 | Ala | Thr | Gln | Ile<br>520 | Thr | Gln | Gly | Pro | Arg<br>525 | Ser | Thr | Ile | |
| GAG | AAG | AAA | GGT | TCC | AGG | GTG | ACC | TTC | ACG | TGC | CAG | GCC | TCC | TTT | GAC | 1632 |
| Glu | Lys<br>530 | Lys | Gly | Ser | Arg | Val<br>535 | Thr | Phe | Thr | Cys | Gln<br>540 | Ala | Ser | Phe | Asp | |
| CCC | TCC | TTG | CAG | CCC | AGC | ATC | ACC | TGG | CGT | GGG | GAC | GGT | CGA | GAC | CTC | 1680 |
| Pro | Ser | Leu<br>545 | Gln | Pro | Ser | Ile | Thr<br>550 | Trp | Arg | Gly | Asp | Gly<br>555 | Arg | Asp | Leu<br>560 | |
| CAG | GAG | CTT | GGG | GAC | AGT | GAC | AAG | TAC | TTC | ATA | GAG | GAT | GGG | CGC | CTG | 1728 |
| Gln | Glu | Leu | Gly | Asp<br>565 | Ser | Asp | Lys | Tyr | Phe<br>570 | Ile | Glu | Asp | Gly | Arg<br>575 | Leu | |
| GTC | ATC | CAC | AGC | CTG | GAC | TAC | AGC | GAC | CAG | GGC | AAC | TAC | AGC | TGC | GTG | 1776 |
| Val | Ile | His | Ser<br>580 | Leu | Asp | Tyr | Ser | Asp<br>585 | Gln | Gly | Asn | Tyr | Ser<br>590 | Cys | Val | |
| GCC | AGT | ACC | GAA | CTG | GAT | GTG | GTG | GAG | AGT | AGG | GCA | CAG | CTC | TTG | GTG | 1824 |
| Ala | Ser | Thr<br>595 | Glu | Leu | Asp | Val<br>600 | Val | Glu | Ser | Arg | Ala<br>605 | Gln | Leu | Leu | Val | |
| GTG | GGG | AGC | CCT | GGG | CCG | GTG | CCA | CGG | CTG | GTG | CTG | TCC | GAC | CTG | CAC | 1872 |
| Val | Gly | Ser<br>610 | Pro | Gly | Pro | Val<br>615 | Pro | Arg | Leu | Val | Leu<br>620 | Ser | Asp | Leu | His | |
| CTG | CTG | ACG | CAG | AGC | CAG | GTG | CGC | GTG | TCC | TGG | AGT | CCT | GCA | GAA | GAC | 1920 |
| Leu | Leu<br>625 | Thr | Gln | Ser | Gln<br>630 | Val | Arg | Val | Ser | Trp<br>635 | Ser | Pro | Ala | Glu | Asp<br>640 | |
| CAC | AAT | GCC | CCC | ATT | GAG | AAA | TAT | GAC | ATT | GAA | TTT | GAG | GAC | AAG | GAA | 1968 |

|   |   |   |   |   |   |   |   |   |   |   |   |   |   |   |   |
|---|---|---|---|---|---|---|---|---|---|---|---|---|---|---|---|
| His | Asn | Ala | Pro | Ile | Glu | Lys | Tyr | Asp | Ile | Glu | Phe | Glu | Asp | Lys | Glu |
|  |  |  |  | 645 |  |  |  | 650 |  |  |  | 655 |  |  |  |

| ATG | GCG | CCT | GAA | AAA | TGG | TAC | AGT | CTG | GGC | AAG | GTT | CCA | GGG | AAC | CAG | 2016 |
|---|---|---|---|---|---|---|---|---|---|---|---|---|---|---|---|---|
| Met | Ala | Pro | Glu | Lys | Trp | Tyr | Ser | Leu | Gly | Lys | Val | Pro | Gly | Asn | Gln |  |
|  |  | 660 |  |  |  |  | 665 |  |  |  |  | 670 |  |  |  |  |

| ACC | TCT | ACC | ACC | CTC | AAG | CTG | TCG | CCC | TAT | GTC | CAC | TAC | ACC | TTT | AGG | 2064 |
|---|---|---|---|---|---|---|---|---|---|---|---|---|---|---|---|---|
| Thr | Ser | Thr | Thr | Leu | Lys | Leu | Ser | Pro | Tyr | Val | His | Tyr | Thr | Phe | Arg |  |
|  |  | 675 |  |  |  |  | 680 |  |  |  |  | 685 |  |  |  |  |

| GTT | ACT | GCC | ATA | AAC | AAA | TAT | GGC | CCC | GGG | GAG | CCC | AGC | CCG | GTC | TCT | 2112 |
|---|---|---|---|---|---|---|---|---|---|---|---|---|---|---|---|---|
| Val | Thr | Ala | Ile | Asn | Lys | Tyr | Gly | Pro | Gly | Glu | Pro | Ser | Pro | Val | Ser |  |
|  | 690 |  |  |  |  | 695 |  |  |  |  | 700 |  |  |  |  |  |

| GAG | ACT | GTG | GTC | ACA | CCT | GAG | GCA | GCC | CCA | GAG | AAG | AAC | CCT | GTG | GAT | 2160 |
|---|---|---|---|---|---|---|---|---|---|---|---|---|---|---|---|---|
| Glu | Thr | Val | Val | Thr | Pro | Glu | Ala | Ala | Pro | Glu | Lys | Asn | Pro | Val | Asp |  |
| 705 |  |  |  |  | 710 |  |  |  |  | 715 |  |  |  |  | 720 |  |

| GTG | AAG | GGG | GAA | GGA | AAT | GAG | ACC | ACC | AAT | ATG | GTC | ATC | ACG | TGG | AAG | 2208 |
|---|---|---|---|---|---|---|---|---|---|---|---|---|---|---|---|---|
| Val | Lys | Gly | Glu | Gly | Asn | Glu | Thr | Thr | Asn | Met | Val | Ile | Thr | Trp | Lys |  |
|  |  |  |  | 725 |  |  |  |  | 730 |  |  |  |  | 735 |  |  |

| CCG | CTC | CGG | TGG | ATG | GAC | TGG | AAC | GCC | CCC | CAG | GTT | CAG | TAC | CGC | GTG | 2256 |
|---|---|---|---|---|---|---|---|---|---|---|---|---|---|---|---|---|
| Pro | Leu | Arg | Trp | Met | Asp | Trp | Asn | Ala | Pro | Gln | Val | Gln | Tyr | Arg | Val |  |
|  |  |  | 740 |  |  |  |  | 745 |  |  |  |  | 750 |  |  |  |

| CAG | TGG | CGC | CCT | CAG | GGG | ACA | CGA | GGG | CCC | TGG | CAG | GAG | CAG | ATT | GTC | 2304 |
|---|---|---|---|---|---|---|---|---|---|---|---|---|---|---|---|---|
| Gln | Trp | Arg | Pro | Gln | Gly | Thr | Arg | Gly | Pro | Trp | Gln | Glu | Gln | Ile | Val |  |
|  |  | 755 |  |  |  |  | 760 |  |  |  |  | 765 |  |  |  |  |

| AGC | GAC | CCC | TTC | CTG | GTG | GTG | TCC | AAC | ACG | TCC | ACC | TTC | GTG | CCC | TAT | 2352 |
|---|---|---|---|---|---|---|---|---|---|---|---|---|---|---|---|---|
| Ser | Asp | Pro | Phe | Leu | Val | Val | Ser | Asn | Thr | Ser | Thr | Phe | Val | Pro | Tyr |  |
|  | 770 |  |  |  |  | 775 |  |  |  |  | 780 |  |  |  |  |  |

| GAG | ATC | AAA | GTC | CAG | GCC | GTC | AAC | AGC | CAG | GGC | AAG | GGA | CCA | GAG | CCC | 2400 |
|---|---|---|---|---|---|---|---|---|---|---|---|---|---|---|---|---|
| Glu | Ile | Lys | Val | Gln | Ala | Val | Asn | Ser | Gln | Gly | Lys | Gly | Pro | Glu | Pro |  |
| 785 |  |  |  |  | 790 |  |  |  |  | 795 |  |  |  |  | 800 |  |

| CAG | GTC | ACT | ATC | GGC | TAC | TCT | GGA | GAG | GAC | TAC | CCC | CAG | GCA | ATC | CCT | 2448 |
|---|---|---|---|---|---|---|---|---|---|---|---|---|---|---|---|---|
| Gln | Val | Thr | Ile | Gly | Tyr | Ser | Gly | Glu | Asp | Tyr | Pro | Gln | Ala | Ile | Pro |  |
|  |  |  |  | 805 |  |  |  |  | 810 |  |  |  |  | 815 |  |  |

| GAG | CTG | GAA | GGC | ATT | GAA | ATC | CTC | AAC | TCA | AGT | GCC | GTG | CTG | GTC | AAG | 2496 |
|---|---|---|---|---|---|---|---|---|---|---|---|---|---|---|---|---|
| Glu | Leu | Glu | Gly | Ile | Glu | Ile | Leu | Asn | Ser | Ser | Ala | Val | Leu | Val | Lys |  |
|  |  |  |  | 820 |  |  |  |  | 825 |  |  |  |  | 830 |  |  |

| TGG | CGG | CCG | GTG | GAC | CTG | GCC | CAG | GTC | AAG | GGC | CAC | CTC | CGC | GGA | TAC | 2544 |
|---|---|---|---|---|---|---|---|---|---|---|---|---|---|---|---|---|
| Trp | Arg | Pro | Val | Asp | Leu | Ala | Gln | Val | Lys | Gly | His | Leu | Arg | Gly | Tyr |  |
|  |  | 835 |  |  |  |  | 840 |  |  |  |  | 845 |  |  |  |  |

| AAT | GTG | ACG | TAC | TGG | AGG | GAG | GGC | AGT | CAG | AGG | AAG | CAC | AGC | AAG | AGA | 2592 |
|---|---|---|---|---|---|---|---|---|---|---|---|---|---|---|---|---|
| Asn | Val | Thr | Tyr | Trp | Arg | Glu | Gly | Ser | Gln | Arg | Lys | His | Ser | Lys | Arg |  |
| 850 |  |  |  |  | 855 |  |  |  |  | 860 |  |  |  |  |  |  |

| CAT | ATC | CAC | AAA | GAC | CAT | GTG | GTG | GTG | CCC | GCC | AAC | ACC | ACC | AGT | GTC | 2640 |
|---|---|---|---|---|---|---|---|---|---|---|---|---|---|---|---|---|
| His | Ile | His | Lys | Asp | His | Val | Val | Val | Pro | Ala | Asn | Thr | Thr | Ser | Val |  |
| 865 |  |  |  |  | 870 |  |  |  |  | 875 |  |  |  |  | 880 |  |

| ATC | CTC | AGT | GGC | TTG | CGG | CCC | TAT | AGC | TCC | TAC | CAC | CTG | GAG | GTG | CAG | 2688 |
|---|---|---|---|---|---|---|---|---|---|---|---|---|---|---|---|---|
| Ile | Leu | Ser | Gly | Leu | Arg | Pro | Tyr | Ser | Ser | Tyr | His | Leu | Glu | Val | Gln |  |
|  |  |  |  | 885 |  |  |  |  | 890 |  |  |  |  | 895 |  |  |

| GCC | TTT | AAC | GGG | CGA | GGA | TCG | GGG | CCC | GCC | AGC | GAG | TTC | ACC | TTC | AGC | 2736 |
|---|---|---|---|---|---|---|---|---|---|---|---|---|---|---|---|---|
| Ala | Phe | Asn | Gly | Arg | Gly | Ser | Gly | Pro | Ala | Ser | Glu | Phe | Thr | Phe | Ser |  |
|  |  |  | 900 |  |  |  |  | 905 |  |  |  |  | 910 |  |  |  |

| ACC | CCA | GAG | GGA | GTG | CCT | GGC | CAC | CCC | GAG | GCG | TTG | CAC | CTG | GAG | TGC | 2784 |
|---|---|---|---|---|---|---|---|---|---|---|---|---|---|---|---|---|
| Thr | Pro | Glu | Gly | Val | Pro | Gly | His | Pro | Glu | Ala | Leu | His | Leu | Glu | Cys |  |
|  |  |  | 915 |  |  |  |  | 920 |  |  |  |  | 925 |  |  |  |

| CAG | TCG | AAC | ACC | AGC | CTG | CTG | CTG | CGC | TGG | CAG | CCC | CCA | CTC | AGC | CAC | 2832 |
|---|---|---|---|---|---|---|---|---|---|---|---|---|---|---|---|---|
| Gln | Ser | Asn | Thr | Ser | Leu | Leu | Leu | Arg | Trp | Gln | Pro | Pro | Leu | Ser | His |  |
|  | 930 |  |  |  |  | 935 |  |  |  |  | 940 |  |  |  |  |  |

| AAC | GGC | GTG | CTC | ACC | GGC | TAC | GTG | CTC | TCC | TAC | CAC | CCC | CTG | GAT | GAG | 2880 |
|---|---|---|---|---|---|---|---|---|---|---|---|---|---|---|---|---|
| Asn | Gly | Val | Leu | Thr | Gly | Tyr | Val | Leu | Ser | Tyr | His | Pro | Leu | Asp | Glu |  |
| 945 |  |  |  |  | 950 |  |  |  |  | 955 |  |  |  |  | 960 |  |

| GGG | GGC | AAG | GGG | CAA | CTG | TCC | TTC | AAC | CTT | CGG | GAC | CCC | GAA | CTT | CGG | 2928 |

```
Gly Gly Lys Gly Gln Leu Ser Phe Asn Leu Arg Asp Pro Glu Leu Arg
            965                 970                 975

ACA CAC AAC CTG ACC GAT CTC AGC CCC CAC CTG CGG TAC CGC TTC CAG    2976
Thr His Asn Leu Thr Asp Leu Ser Pro His Leu Arg Tyr Arg Phe Gln
            980                 985                 990

CTT CAG GCC ACC ACC AAA GAG GGC CCT GGT GAA GCC ATC GTA CGG GAA    3024
Leu Gln Ala Thr Thr Lys Glu Gly Pro Gly Glu Ala Ile Val Arg Glu
            995                 1000                1005

GGA GGC ACT ATG GCC TTG TCT GGG ATC TCA GAT TTT GGC AAC ATC TCA    3072
Gly Gly Thr Met Ala Leu Ser Gly Ile Ser Asp Phe Gly Asn Ile Ser
            1010                1015                1020

GCC ACA GCG GGT GAA AAC TAC AGT GTC GTC TCC TGG GTC CCC AAG GAG    3120
Ala Thr Ala Gly Glu Asn Tyr Ser Val Val Ser Trp Val Pro Lys Glu
1025                1030                1035                1040

GGC CAG TGC AAC TTC AGG TTC CAT ATC TTG TTC AAA GCC TTG GGA GAA    3168
Gly Gln Cys Asn Phe Arg Phe His Ile Leu Phe Lys Ala Leu Gly Glu
                1045                1050                1055

GAG AAG GGT GGG GCT TCC CTT TCG CCA CAG TAT GTC AGC TAC AAC CAG    3216
Glu Lys Gly Gly Ala Ser Leu Ser Pro Gln Tyr Val Ser Tyr Asn Gln
            1060                1065                1070

AGC TCC TAC ACG CAG TGG GAC CTG CAG CCT GAC ACT GAC TAC GAG ATC    3264
Ser Ser Tyr Thr Gln Trp Asp Leu Gln Pro Asp Thr Asp Tyr Glu Ile
            1075                1080                1085

CAC TTG TTT AAG GAG AGG ATG TTC CGG CAC CAA ATG GCT GTG AAG ACC    3312
His Leu Phe Lys Glu Arg Met Phe Arg His Gln Met Ala Val Lys Thr
            1090                1095                1100

AAT GGC ACA GGC CGC GTG AGG CTC CCT CCT GCT GGC TTC GCC ACT GAG    3360
Asn Gly Thr Gly Arg Val Arg Leu Pro Pro Ala Gly Phe Ala Thr Glu
1105                1110                1115                1120

GGC TGG TTC ATC GGC TTT GTG AGT GCC ATC ATC CTC CTG CTC CTC GTC    3408
Gly Trp Phe Ile Gly Phe Val Ser Ala Ile Ile Leu Leu Leu Leu Val
                1125                1130                1135

CTG CTC ATC CTC TGC TTC ATC AAG CGC AGC AAG GGC GGC AAA TAC TCA    3456
Leu Leu Ile Leu Cys Phe Ile Lys Arg Ser Lys Gly Gly Lys Tyr Ser
                1140                1145                1150

GTG AAG GAT AAG GAG GAC ACC CAG GTG GAC TCT GAG GCC CGA CCG ATG    3504
Val Lys Asp Lys Glu Asp Thr Gln Val Asp Ser Glu Ala Arg Pro Met
            1155                1160                1165

AAA GAT GAG ACC TTC GGC GAG TAC AGG TCC CTG GAG AGT GAC AAC GAG    3552
Lys Asp Glu Thr Phe Gly Glu Tyr Arg Ser Leu Glu Ser Asp Asn Glu
            1170                1175                1180

GAG AAG GCC TTT GGC AGC AGC CAG CCA TCG CTC AAC GGG GAC ATC AAG    3600
Glu Lys Ala Phe Gly Ser Ser Gln Pro Ser Leu Asn Gly Asp Ile Lys
1185                1190                1195                1200

CCC CTG GGC AGT GAC GAC AGC CTG GCC GAT TAT GGG GGC AGC GTG GAT    3648
Pro Leu Gly Ser Asp Asp Ser Leu Ala Asp Tyr Gly Gly Ser Val Asp
                1205                1210                1215

GTT CAG TTC AAC GAG GAT GGT TCG TTC ATT GGC CAG TAC AGT GGC AAG    3696
Val Gln Phe Asn Glu Asp Gly Ser Phe Ile Gly Gln Tyr Ser Gly Lys
                1220                1225                1230

AAG GAG AAG GAG GCG GCA GGG GGC AAT GAC AGC TCA GGG GCC ACT TCC    3744
Lys Glu Lys Glu Ala Ala Gly Gly Asn Asp Ser Ser Gly Ala Thr Ser
            1235                1240                1245

CCC ATC AAC CCT GCC GTG GCC CTA GAA TAG                            3774
Pro Ile Asn Pro Ala Val Ala Leu Glu
            1250                1255
```

( 2 ) INFORMATION FOR SEQ ID NO: 2:

( i ) SEQUENCE CHARACTERISTICS:
        ( A ) LENGTH: 50
        ( B ) TYPE: nucleic acid (C) STRANDEDNESS: single
(D) TOPOLOGY: linear (ii) MOLECULE TYPE: oligonucleotide (iii) HYPOTHETICAL: irrelevant (iv) ANTI-SENSE: no (vi) ORIGINAL SOURCE:
(A) ORGANISM: mouse (x) SEQUENCE DESCRIPTION: SEQ ID NO: 2:

GAGGACACCC AGGTGGACTC TGAGGCCCGA CCGATGAAAG ATGAGACCTT    50

(2) INFORMATION FOR SEQ ID NO: 3:

(i) SEQUENCE CHARACTERISTICS:
(A) LENGTH: 40
(B) TYPE: nucleic acid
(C) STRANDEDNESS: single
(D) TOPOLOGY: linear (ii) MOLECULE TYPE: oligonucleotide (iii) HYPOTHETICAL: irrelevant (iv) ANTI-SENSE: no (x) SEQUENCE DESCRIPTION: SEQ ID NO: 3:

TGCCACGCCC ACTTCCCAGG CACCAGGACC ATCATTCAGA    40

(2) INFORMATION FOR SEQ ID NO: 4:

(i) SEQUENCE CHARACTERISTICS:
(A) LENGTH: 95
(B) TYPE: amino acid
(C) STRANDEDNESS: single
(D) TOPOLOGY: linear (ii) MOLECULE TYPE: amino acids (iii) HYPOTHETICAL: irrelevant (iv) ANTI-SENSE: no (vi) ORIGINAL SOURCE:
(A) ORGANISM: mouse
(B) INDIVIDUAL ISOLATE: 8 day old mouse brain (vii) IMMEDIATE SOURCE:
(A) LIBRARY: lamda GT 10 and lamda GT11
(B) CLONE: synthesis of several clones (x) PUBLICATION INFORMATION:
(A) AUTHORS: Moos, M.
Tacke, R.
Scherer, H.
Teplow, D.
Fruh, K.
Schachner, M.
(B) TITLE: Neural adhesion molecule L1 is a
member of the immunoglobulin
superfamily with binding domains
similar to fibronectin
(C) JOURNAL: NATURE
(D) VOLUME: 334
(E) ISSUE:
(F) PAGES: 701-703
(G) DATE: 1988

(xi) SEQUENCE DESCRIPTION: SEQ ID NO: 4:

Val Ile Thr Glu Gln Ser Pro Arg Arg Leu Val Val Phe Pro Thr Asp Asp
1               5                   10                  15

```
Ile Ser Leu Lys Cys Glu Ala Arg Gly Arg Pro Gln Val Glu Phe Arg Trp
        20              25              30

Thr Lys Asp Gly Ile His Phe Lys Pro Lys Glu Glu Leu Gly Val Val Val
35              40              45              50

His Glu Ala Pro Tyr Ser Gly Ser Phe Thr Ile Glu Gly Asn Asn Ser Phe
            55              60              65

Ala Gln Arg Phe Gln Gly Ile Tyr Arg Cys Tyr Ala Ser Asn Lys Leu Gly
    70              75              80              85

Thr Ala Met Ser His Glu Ile Gln Leu Val
            90              95
```

(2) INFORMATION FOR SEQ ID NO: 5:

(i) SEQUENCE CHARACTERISTICS:
        (A) LENGTH: 106
        (B) TYPE: amino acid
        (C) STRANDEDNESS: single
        (D) TOPOLOGY: linear (ii) MOLECULE TYPE: amino acids (iii) HYPOTHETICAL: irrelevant (iv) ANTI-SENSE: no (vi) ORIGINAL SOURCE:
        (A) ORGANISM: mouse
        (B) INDIVIDUAL ISOLATE: 8 day old mouse brain (vii) IMMEDIATE SOURCE:
        (A) LIBRARY: lamda GT 10 and lamda GT11
        (B) CLONE: synthesis of several clones (x) PUBLICATION INFORMATION:
        (A) AUTHORS: Moos, M.
            Tacke, R.
            Scherer, H.
            Teplow, D.
            Fruh, K.
            Schachner, M.
        (B) TITLE: Neural adhesion molecule L1 is a
            member of the immunoglobulin
            superfamily with binding domains
            similar to fibronectin
        (C) JOURNAL: NATURE
        (D) VOLUME: 334
        (E) ISSUE:
        (F) PAGES: 701-703
        (G) DATE: 1988

(xi) SEQUENCE DESCRIPTION: SEQ ID NO: 5:

```
Ala Glu Gly Ala Pro Lys Trp Pro Lys Glu Thr Val Lys Pro Val Glu Val
1               5               10              15

Glu Glu Gly Glu Ser Val Val Leu Pro Cys Asn Pro Pro Ser Ala Ala
        20              25              30

Pro Pro Arg Ile Tyr Trp Met Asn Ser Lys Ile Phe Asp Ile Lys Gln Asp
35              40              45              50

Glu Arg Val Ser Met Gly Gln Asn Gly Asp Leu Tyr Phe Ala Asn Val Leu
            55              60              65

Thr Ser Asp Asn His Ser Asp Tyr Ile Cys Asn Ala His Phe Pro Gly Thr
    70              75              80              85

Arg Thr Ile Ile Gln Lys Glu Pro Ile Asp Leu Arg Val Lys Pro Thr Asn
            90              95              100

Ser Met Ile Asp
        105
```

(2) INFORMATION FOR SEQ ID NO: 6:

( i ) SEQUENCE CHARACTERISTICS:
    ( A ) LENGTH: 96
    ( B ) TYPE: amino acid
    ( C ) STRANDEDNESS: single
    ( D ) TOPOLOGY: linear ( i i ) MOLECULE TYPE: amino acids ( i i i ) HYPOTHETICAL: irrelevant ( i v ) ANTI-SENSE: no ( v i ) ORIGINAL SOURCE:
    ( A ) ORGANISM: mouse
    ( B ) INDIVIDUAL ISOLATE: 8 day old mouse brain ( v i i ) IMMEDIATE SOURCE:
    ( A ) LIBRARY: lamda GT 10 and lamda GT11
    ( B ) CLONE: synthesis of several clones ( x ) PUBLICATION INFORMATION:
    ( A ) AUTHORS: Moos, M.
        Tacke, R.
        Scherer, H.
        Teplow, D.
        Fruh, K.
        Schachner, M.
    ( B ) TITLE: Neural adhesion molecule L1 is a member of the immunoglobulin superfamily with binding domains similar to fibronectin
    ( C ) JOURNAL: NATURE
    ( D ) VOLUME: 334
    ( E ) ISSUE:
    ( F ) PAGES: 701-703
    ( G ) DATE: 1988

( x i ) SEQUENCE DESCRIPTION: SEQ ID NO: 6:

```
Arg  Lys  Pro  Arg  Leu  Leu  Phe  Pro  Thr  Asn  Ser  Ser  Ser  Arg  Leu  Val  Ala
1                   5                        10                       15

Leu  Gln  Gly  Gln  Ser  Leu  Ile  Leu  Glu  Cys  Ile  Ala  Glu  Gly  Phe  Pro  Thr
          20                      25                      30

Pro  Thr  Ile  Lys  Trp  Leu  His  Pro  Ser  Asp  Pro  Met  Pro  Thr  Asp  Arg  Val
35                       40                      45                           50

Ile  Tyr  Gln  Asn  His  Asn  Lys  Thr  Leu  Gln  Leu  Leu  Asn  Val  Gly  Glu  Glu
               55                       60                      65

Asp  Asp  Gly  Glu  Tyr  Thr  Cys  Leu  Ala  Glu  Asn  Ser  Leu  Gly  Ser  Ala  Arg
     70                       75                      80                           85

His  Ala  Tyr  Tyr  Val  Thr  Val  Glu  Ala  Ala  Pro
               90                      95
```

( 2 ) INFORMATION FOR SEQ ID NO: 7:

( i ) SEQUENCE CHARACTERISTICS:
        ( A ) LENGTH: 92
        ( B ) TYPE: amino acid
        ( C ) STRANDEDNESS: single
        ( D ) TOPOLOGY: linear ( i i ) MOLECULE TYPE: amino acids ( i i i ) HYPOTHETICAL: irrelevant ( i v ) ANTI-SENSE: no ( v i ) ORIGINAL SOURCE:
        ( A ) ORGANISM: mouse
        ( B ) INDIVIDUAL ISOLATE: 8 day old mouse brain ( v i i ) IMMEDIATE SOURCE:
        ( A ) LIBRARY: lamda GT 10 and lamda GT11
        ( B ) CLONE: synthesis of several clones (x) PUBLICATION INFORMATION:
    (A) AUTHORS: Moos, M.
                 Tacke, R.
                 Scherer, H.
                 Teplow, D.
                 Fruh, K.
                 Schachner, M.
    (B) TITLE: Neural adhesion molecule L1 is a
               member of the immunoglobulin
               superfamily with binding domains
               similar to fibronectin
    (C) JOURNAL: NATURE
    (D) VOLUME: 334
    (E) ISSUE:
    (F) PAGES: 701-703
    (G) DATE: 1988

(xi) SEQUENCE DESCRIPTION: SEQ ID NO: 7:

| Tyr | Trp | Leu | Gln | Lys | Pro | Gln | Ser | His | Leu | Tyr | Gly | Pro | Gly | Glu | Thr | Ala |
|-----|-----|-----|-----|-----|-----|-----|-----|-----|-----|-----|-----|-----|-----|-----|-----|-----|
| 1   |     |     |     | 5   |     |     |     |     | 10  |     |     |     | 15  |     |     |     |

| Arg | Leu | Asp | Cys | Gln | Val | Gln | Gly | Arg | Pro | Gln | Pro | Glu | Ile | Thr | Trp | Arg |
|-----|-----|-----|-----|-----|-----|-----|-----|-----|-----|-----|-----|-----|-----|-----|-----|-----|
|     | 20  |     |     |     | 25  |     |     |     |     | 30  |     |     |     |     |     |     |

| Ile | Asn | Gly | Met | Ser | Met | Glu | Thr | Val | Asn | Lys | Asp | Gln | Lys | Tyr | Arg | Ile |
|-----|-----|-----|-----|-----|-----|-----|-----|-----|-----|-----|-----|-----|-----|-----|-----|-----|
| 35  |     |     |     |     | 40  |     |     |     |     | 45  |     |     |     |     | 50  |     |

| Glu | Gln | Gly | Ser | Leu | Ile | Leu | Ser | Asn | Val | Gln | Pro | Thr | Asp | Thr | Met | Val |
|-----|-----|-----|-----|-----|-----|-----|-----|-----|-----|-----|-----|-----|-----|-----|-----|-----|
|     |     |     | 55  |     |     |     |     | 60  |     |     |     |     | 65  |     |     |     |

| Thr | Gln | Cys | Glu | Ala | Arg | Asn | Gln | His | Gly | Leu | Leu | Leu | Ala | Asn | Ala | Tyr |
|-----|-----|-----|-----|-----|-----|-----|-----|-----|-----|-----|-----|-----|-----|-----|-----|-----|
|     | 70  |     |     |     |     | 75  |     |     |     |     |     | 80  |     |     |     | 85  |

| Ile | Tyr | Val | Val | Gln | Leu | Pro |
|-----|-----|-----|-----|-----|-----|-----|
|     |     |     |     | 90  |     |     |

(2) INFORMATION FOR SEQ ID NO: 8:

(i) SEQUENCE CHARACTERISTICS:
        (A) LENGTH: 93
        (B) TYPE: amino acid
        (C) STRANDEDNESS: single
        (D) TOPOLOGY: linear (ii) MOLECULE TYPE: amino acids (iii) HYPOTHETICAL: irrelevant (iv) ANTI-SENSE: no (vi) ORIGINAL SOURCE:
         (A) ORGANISM: mouse
         (B) INDIVIDUAL ISOLATE: 8 day old mouse brain (vii) IMMEDIATE SOURCE:
          (A) LIBRARY: lamda GT 10 and lamda GT11
          (B) CLONE: synthesis of several clones (x) PUBLICATION INFORMATION:
        (A) AUTHORS: Moos, M.
                     Tacke, R.
                     Scherer, H.
                     Teplow, D.
                     Fruh, K.
                     Schachner, M.
        (B) TITLE: Neural adhesion molecule L1 is a
                   member of the immunoglobulin
                   superfamily with binding domains
                   similar to fibronectin
        (C) JOURNAL: NATURE
        (D) VOLUME: 334
        (E) ISSUE:
        (F) PAGES: 701-703
        (G) DATE: 1988

(xi) SEQUENCE DESCRIPTION: SEQ ID NO: 8:

| Ala | Arg | Ile | Leu | Thr | Lys | Asp | Asn | Gln | Thr | Tyr | Met | Ala | Val | Glu | Gly | Ser |
|-----|-----|-----|-----|-----|-----|-----|-----|-----|-----|-----|-----|-----|-----|-----|-----|-----|
| 1   |     |     |     | 5   |     |     |     |     | 10  |     |     |     |     | 15  |     |     |

|     |     |     |     |     |     |     |     |     |     |     |     |     |     |     |
|-----|-----|-----|-----|-----|-----|-----|-----|-----|-----|-----|-----|-----|-----|-----|
| Thr | Ala | Tyr<br>20 | Leu | Leu | Cys | Lys | Ala<br>25 | Phe | Gly | Ala | Pro<br>30 | Val | Pro | Ser | Val | Gln |
| Trp<br>35 | Leu | Asp | Glu | Glu<br>40 | Gly | Thr | Thr | Val | Leu | Gln<br>45 | Asp | Glu | Arg | Phe | Phe<br>50 | Pro |
| Tyr | Ala | Asn | Gly<br>55 | Thr | Leu | Ser | Ile | Arg<br>60 | Asp | Leu | Gln | Ala | Asn<br>65 | Asp | Thr | Gly |
| Arg | Tyr<br>70 | Phe | Cys | Gln | Ala<br>75 | Ala | Asn | Asp | Gln | Asn<br>80 | Asn | Val | Ile | Ile | Leu | Ala<br>85 |
| Asn | Leu | Gln | Val | Lys<br>90 | Glu | Ala | Thr |

( 2 ) INFORMATION FOR SEQ ID NO: 9:

( i ) SEQUENCE CHARACTERISTICS:
        ( A ) LENGTH: 96
        ( B ) TYPE: amino acid
        ( C ) STRANDEDNESS: single
        ( D ) TOPOLOGY: linear ( i i ) MOLECULE TYPE: amino acids ( i i i ) HYPOTHETICAL: irrelevant ( i v ) ANTI-SENSE: no ( v i ) ORIGINAL SOURCE:
        ( A ) ORGANISM: mouse
        ( B ) INDIVIDUAL ISOLATE: 8 day old mouse brain ( v i i ) IMMEDIATE SOURCE:
        ( A ) LIBRARY: lamda GT 10 and lamda GT11
        ( B ) CLONE: synthesis of several clones ( x ) PUBLICATION INFORMATION:
        ( A ) AUTHORS: Moos, M.
                Tacke, R.
                Scherer, H.
                Teplow, D.
                Fruh, K.
                Schachner, M.
        ( B ) TITLE: Neural adhesion molecule L1 is a
                member of the immunoglobulin
                superfamily with binding domains
                similar to fibronectin
        ( C ) JOURNAL: NATURE
        ( D ) VOLUME: 334
        ( E ) ISSUE:
        ( F ) PAGES: 701-703
        ( G ) DATE: 1988

( x i ) SEQUENCE DESCRIPTION: SEQ ID NO: 9:

|     |     |     |     |     |     |     |     |     |     |     |     |     |     |     |     |     |
|-----|-----|-----|-----|-----|-----|-----|-----|-----|-----|-----|-----|-----|-----|-----|-----|-----|
| Gln<br>1 | Ile | Thr | Gln | Gly<br>5 | Pro | Arg | Ser | Ala | Ile<br>10 | Glu | Lys | Lys | Gly | Ala<br>15 | Arg | Val |
| Thr | Phe | Thr<br>20 | Cys | Gln | Ala | Ser | Phe<br>25 | Asp | Pro | Ser | Leu | Gln<br>30 | Ala | Ser | Ile | Thr |
| Trp<br>35 | Arg | Gly | Asp | Gly<br>40 | Arg | Asp | Leu | Gln | Glu<br>45 | Arg | Gly | Asp | Ser | Asp | Lys<br>50 | Tyr |
| Phe | Ile | Glu | Asp<br>55 | Gly | Lys | Leu | Val | Ile<br>60 | Gln | Ser | Leu | Asp | Tyr<br>65 | Ser | Asp | Gln |
| Gly | Asn<br>70 | Tyr | Ser | Cys | Val | Ala<br>75 | Ser | Thr | Glu | Leu | Asp<br>80 | Glu | Val | Glu | Ser | Arg<br>85 |
| Ala | Gln | Leu | Leu | Val<br>90 | Val | Gly | Ser | Pro | Gly<br>95 | Pro |

( 2 ) INFORMATION FOR SEQ ID NO: 10:

( i ) SEQUENCE CHARACTERISTICS:
        ( A ) LENGTH: 101

(B) TYPE: amino acid
                (C) STRANDEDNESS: single
                (D) TOPOLOGY: linear (ii) MOLECULE TYPE: amino acids (iii) HYPOTHETICAL: irrelevant (iv) ANTI-SENSE: no (vi) ORIGINAL SOURCE:
                (A) ORGANISM: mouse
                (B) INDIVIDUAL ISOLATE: 8 day old mouse brain (vii) IMMEDIATE SOURCE:
                (A) LIBRARY: lamda GT 10 and lamda GT11
                (B) CLONE: synthesis of several clones (x) PUBLICATION INFORMATION:
                (A) AUTHORS: Moos, M.
                        Tacke, R.
                        Scherer, H.
                        Teplow, D.
                        Fruh, K.
                        Schachner, M.
                (B) TITLE: Neural adhesion molecule L1 is a
                        member of the immunoglobulin
                        superfamily with binding domains
                        similar to fibronectin
                (C) JOURNAL: NATURE
                (D) VOLUME: 334
                (E) ISSUE:
                (F) PAGES: 701-703
                (G) DATE: 1988

(xi) SEQUENCE DESCRIPTION: SEQ ID NO: 10:

```
Val Pro His Leu Glu Leu Ser Asp Arg His Leu Leu Lys Gln Ser Gln Val
 1               5                  10                  15

His Leu Ser Trp Ser Pro Ala Glu Asp His Asn Ser Pro Ile Glu Lys Tyr
            20                  25                  30

Asp Ile Glu Phe Glu Asp Lys Glu Met Ala Pro Glu Lys Trp Phe Ser Leu
 35                  40                  45                  50

Gly Lys Val Pro Gly Asn Gln Thr Ser Thr Thr Leu Lys Leu Ser Pro Tyr
            55                  60                  65

Val His Tyr Thr Phe Arg Val Thr Ala Ile Asn Lys Tyr Gly Pro Gly Glu
    70                  75                  80                  85

Pro Ser Pro Val Ser Glu Ser Val Val Thr Pro Glu Ala Ala Pro Glu
                90                  95                  100
```

(2) INFORMATION FOR SEQ ID NO: 11:

(i) SEQUENCE CHARACTERISTICS:
                (A) LENGTH: 96
                (B) TYPE: amino acid
                (C) STRANDEDNESS: single
                (D) TOPOLOGY: linear (ii) MOLECULE TYPE: amino acids (iii) HYPOTHETICAL: irrelevant (iv) ANTI-SENSE: no (vi) ORIGINAL SOURCE:
                (A) ORGANISM: mouse
                (B) INDIVIDUAL ISOLATE: 8 day old mouse brain (vii) IMMEDIATE SOURCE:
                (A) LIBRARY: lamda GT 10 and lamda GT11
                (B) CLONE: synthesis of several clones (x) PUBLICATION INFORMATION:
                (A) AUTHORS: Moos, M.

Tacke, R.
Scherer, H.
Teplow, D.
Fruh, K.
Schachner, M.
(B) TITLE: Neural adhesion molecule L1 is a
member of the immunoglobulin
superfamily with binding domains
similar to fibronectin
(C) JOURNAL: NATURE
(D) VOLUME: 334
(E) ISSUE:
(F) PAGES: 701-703
(G) DATE: 1988

(xi) SEQUENCE DESCRIPTION: SEQ ID NO: 11:

| Lys | Asn | Pro | Val | Asp | Val | Arg | Gly | Glu | Gly | Asn | Glu | Thr | Asn | Asn | Met | Val |
|---|---|---|---|---|---|---|---|---|---|---|---|---|---|---|---|---|
| 1 | | | | 5 | | | | | 10 | | | | | 15 | | |

| Ile | Thr | Trp | Lys | Pro | Leu | Arg | Trp | Met | Asp | Trp | Asn | Ala | Pro | Gln | Ile | Gln |
|---|---|---|---|---|---|---|---|---|---|---|---|---|---|---|---|---|
| 20 | | | | | 25 | | | | | 30 | | | | | | |

| Tyr | Arg | Val | Gln | Trp | Arg | Pro | Gln | Gly | Lys | Gln | Glu | Thr | Trp | Arg | Lys | Gln |
|---|---|---|---|---|---|---|---|---|---|---|---|---|---|---|---|---|
| 35 | | | | | 40 | | | | | 45 | | | | | 50 | |

| Thr | Val | Ser | Asp | Pro | Phe | Leu | Val | Val | Ser | Asn | Thr | Ser | Thr | Phe | Val | Pro |
|---|---|---|---|---|---|---|---|---|---|---|---|---|---|---|---|---|
| 55 | | | | | 60 | | | | | 65 | | | | | | |

| Tyr | Glu | Ile | Lys | Val | Gln | Ala | Val | Asn | Asn | Gln | Gly | Lys | Gly | Pro | Glu | Pro |
|---|---|---|---|---|---|---|---|---|---|---|---|---|---|---|---|---|
| 70 | | | | | 75 | | | | | 80 | | | | | 85 | |

| Gln | Val | Thr | Ile | Gly | Tyr | Ser | Gly | Glu | Asp | Tyr |
|---|---|---|---|---|---|---|---|---|---|---|
| 90 | | | | | 95 | | | | | |

(2) INFORMATION FOR SEQ ID NO: 12:

(i) SEQUENCE CHARACTERISTICS:
(A) LENGTH: 106
(B) TYPE: amino acid
(C) STRANDEDNESS: single
(D) TOPOLOGY: linear (ii) MOLECULE TYPE: amino acids (iii) HYPOTHETICAL: irrelevant (iv) ANTI-SENSE: no (vi) ORIGINAL SOURCE:
(A) ORGANISM: mouse
(B) INDIVIDUAL ISOLATE: 8 day old mouse brain (vii) IMMEDIATE SOURCE:
(A) LIBRARY: lamda GT 10 and lamda GT11
(B) CLONE: synthesis of several clones (x) PUBLICATION INFORMATION:
(A) AUTHORS: Moos, M.
Tacke, R.
Scherer, H.
Teplow, D.
Fruh, K.
Schachner, M.
(B) TITLE: Neural adhesion molecule L1 is a
member of the immunoglobulin
superfamily with binding domains
similar to fibronectin
(C) JOURNAL: NATURE
(D) VOLUME: 334
(E) ISSUE:
(F) PAGES: 701-703
(G) DATE: 1988

(xi) SEQUENCE DESCRIPTION: SEQ ID NO: 12:

| Pro | Gln | Val | Ser | Pro | Glu | Leu | Glu | Asp | Ile | Thr | Ile | Phe | Asn | Ser | Ser | Thr |
|---|---|---|---|---|---|---|---|---|---|---|---|---|---|---|---|---|
| 1 | | | | 5 | | | | | 10 | | | | | 15 | | |

```
Val Leu Val Arg Trp Arg Pro Val Asp Leu Ala Gln Val Lys Gly His Leu
        20              25              30
Lys Gly Tyr Asn Val Thr Tyr Trp Trp Lys Gly Ser Gln Arg Lys His Ser
 35              40              45              50
Lys Arg His Ile His Lys Ser His Ile Val Val Pro Ala Asn Thr Thr Ser
            55              60              65
Ala Ile Leu Ser Gly Leu Arg Pro Tyr Ser Ser Tyr His Val Glu Val Gln
     70              75              80              85
Ala Phe Asn Gly Arg Gly Leu Gly Pro Ala Ser Glu Trp Thr Phe Ser Thr
                90              95              100
Pro Glu Gly Val
           105
```

( 2 ) INFORMATION FOR SEQ ID NO: 13:

( i ) SEQUENCE CHARACTERISTICS:
        ( A ) LENGTH: 98
        ( B ) TYPE: amino acid
        ( C ) STRANDEDNESS: single
        ( D ) TOPOLOGY: linear ( i i ) MOLECULE TYPE: amino acids ( i i i ) HYPOTHETICAL: irrelevant ( i v ) ANTI-SENSE: no ( v i ) ORIGINAL SOURCE:
        ( A ) ORGANISM: mouse
        ( B ) INDIVIDUAL ISOLATE: 8 day old mouse brain ( v i i ) IMMEDIATE SOURCE:
        ( A ) LIBRARY: lamda GT 10 and lamda GT11
        ( B ) CLONE: synthesis of several clones ( x ) PUBLICATION INFORMATION:
        ( A ) AUTHORS: Moos, M.
                Tacke, R.
                Scherer, H.
                Teplow, D.
                Fruh, K.
                Schachner, M.
        ( B ) TITLE: Neural adhesion molecule L1 is a
                member of the immunoglobulin
                superfamily with binding domains
                similar to fibronectin
        ( C ) JOURNAL: NATURE
        ( D ) VOLUME: 334
        ( E ) ISSUE:
        ( F ) PAGES: 701-703
        ( G ) DATE: 1988

( x i ) SEQUENCE DESCRIPTION: SEQ ID NO: 13:

```
Pro Gly His Pro Glu Ala Leu His Leu Glu Cys Gln Ser Asp Thr Ser Leu
 1               5               10              15
Leu Leu His Trp Gln Pro Pro Leu Ser His Asn Gly Val Leu Thr Gly Tyr
        20              25              30
Leu Leu Ser Tyr His Pro Val Glu Gly Glu Ser Lys Glu Gln Leu Phe Phe
 35              40              45              50
Asn Leu Ser Asp Pro Glu Leu Arg Thr His Asn Leu Thr Asn Leu Asn Pro
            55              60              65
Asp Leu Gln Tyr Arg Phe Gln Leu Gln Ala Thr Thr Gln Gln Gly Gly Pro
     70              75              80              85
Gly Glu Ala Ile Val Arg Glu Gly Gly Thr Met Ala Leu
                90              95
```

( 2 ) INFORMATION FOR SEQ ID NO: 14:

( i ) SEQUENCE CHARACTERISTICS:
    ( A ) LENGTH: 101
    ( B ) TYPE: amino acid
    ( C ) STRANDEDNESS: single
    ( D ) TOPOLOGY: linear ( i i ) MOLECULE TYPE: amino acids ( i i i ) HYPOTHETICAL: irrelevant ( i v ) ANTI-SENSE: no ( v i ) ORIGINAL SOURCE:
    ( A ) ORGANISM: mouse
    ( B ) INDIVIDUAL ISOLATE: 8 day old mouse brain ( v i i ) IMMEDIATE SOURCE:
    ( A ) LIBRARY: lamda GT 10 and lamda GT11
    ( B ) CLONE: synthesis of several clones ( x ) PUBLICATION INFORMATION:
    ( A ) AUTHORS: Moos, M.
                 Tacke, R.
                 Scherer, H.
                 Teplow, D.
                 Fruh, K.
                 Schachner, M.
    ( B ) TITLE: Neural adhesion molecule L1 is a
               member of the immunoglobulin
               superfamily with binding domains
               similar to fibronectin
    ( C ) JOURNAL: NATURE
    ( D ) VOLUME: 334
    ( E ) ISSUE:
    ( F ) PAGES: 701-703
    ( G ) DATE: 1988

( x i ) SEQUENCE DESCRIPTION: SEQ ID NO: 14:

```
Phe  Gly  Lys  Pro  Asp  Phe  Gly  Asn  Ile  Ser  Ala  Thr  Ala  Gly  Glu  Asn  Tyr
1                   5                        10                       15

Ser  Val  Val  Ser  Trp  Val  Pro  Arg  Lys  Gly  Gln  Cys  Asn  Phe  Arg  Phe  His
          20                      25                       30

Ile  Leu  Phe  Lys  Ala  Leu  Pro  Glu  Gly  Lys  Val  Ser  Pro  Asp  His  Gln  Pro
35                      40                       45                            50

Gln  Pro  Gln  Tyr  Val  Ser  Tyr  Asn  Gln  Ser  Ser  Tyr  Thr  Gln  Trp  Asn  Leu
               55                      60                            65

Gln  Pro  Asp  Thr  Lys  Tyr  Glu  Ile  His  Leu  Ile  Lys  Glu  Lys  Val  Leu  Leu
     70                      75                       80                            85

His  His  Leu  Asp  Val  Lys  Thr  Asn  Gly  Thr  Gly  Pro  Val  Arg  Val  Ser
                    90                            95                       100
```

( 2 ) INFORMATION FOR SEQ ID NO: 15:

( i ) SEQUENCE CHARACTERISTICS:
        ( A ) LENGTH: 145
        ( B ) TYPE: amino acid
        ( C ) STRANDEDNESS: single
        ( D ) TOPOLOGY: linear ( i i ) MOLECULE TYPE: amino acids ( i i i ) HYPOTHETICAL: irrelevant ( i v ) ANTI-SENSE: no ( v i ) ORIGINAL SOURCE:
        ( A ) ORGANISM: mouse
        ( B ) INDIVIDUAL ISOLATE: 8 day old mouse brain ( v i i ) IMMEDIATE SOURCE:
        ( A ) LIBRARY: lamda GT 10 and lamda GT11
        ( B ) CLONE: synthesis of several clones ( x ) PUBLICATION INFORMATION:
- ( A ) AUTHORS: Moos, M.
  Tacke, R.
  Scherer, H.
  Teplow, D.
  Fruh, K.
  Schachner, M.
- ( B ) TITLE: Neural adhesion molecule L1 is a member of the immunoglobulin superfamily with binding domains similar to fibronectin
- ( C ) JOURNAL: NATURE
- ( D ) VOLUME: 334
- ( E ) ISSUE:
- ( F ) PAGES: 701-703
- ( G ) DATE: 1988

( x i ) SEQUENCE DESCRIPTION: SEQ ID NO: 15:

| Thr | Thr | Gly | Ser | Phe | Ala | Ser | Glu | Gly | Trp | Phe | Ile | Ala | Phe | Val | Ser | Ala |
|---|---|---|---|---|---|---|---|---|---|---|---|---|---|---|---|---|
| 1 | | | | 5 | | | | | 10 | | | | | 15 | | |
| Ile | Ile | Leu | Leu | Leu | Leu | Ile | Leu | Leu | Ile | Leu | Cys | Phe | Ile | Lys | Arg | Ser |
| | | 20 | | | | | 25 | | | | | 30 | | | | |
| Lys | Gly | Gly | Lys | Tyr | Ser | Val | Lys | Asp | Lys | Glu | Asp | Thr | Gln | Val | Asp | Ser |
| 35 | | | | | 40 | | | | | 45 | | | | | 50 | |
| Glu | Ala | Arg | Pro | Met | Lys | Asp | Glu | Thr | Phe | Gly | Glu | Tyr | Arg | Ser | Leu | Glu |
| | | | 55 | | | | | 60 | | | | | 65 | | | |
| Ser | Asp | Asn | Glu | Glu | Lys | Ala | Phe | Gly | Ser | Ser | Gln | Pro | Ser | Leu | Asn | Gly |
| | 70 | | | | | 75 | | | | | 80 | | | | | 85 |
| Asp | Ile | Lys | Pro | Leu | Gly | Ser | Asp | Asp | Ser | Leu | Ala | Asp | Tyr | Gly | Gly | Ser |
| | | | | 90 | | | | | 95 | | | | | 100 | | |
| Val | Asp | Val | Gln | Phe | Asn | Glu | Asp | Gly | Ser | Phe | Ile | Gly | Gln | Tyr | Ser | Gly |
| | | 105 | | | | | 110 | | | | | 115 | | | | |
| Lys | Lys | Glu | Lys | Glu | Ala | Ala | Gly | Gly | Asn | Asp | Ser | Ser | Gly | Ala | Thr | Ser |
| 120 | | | | | 125 | | | | | 130 | | | | | 135 | |
| Pro | Ile | Asn | Pro | Ala | Val | Ala | Leu | Glu | | | | | | | | |
| | | | 140 | | | | | 145 | | | | | | | | |

( 2 ) INFORMATION FOR SEQ ID NO:16:

- ( i ) SEQUENCE CHARACTERISTICS:
  - ( A ) LENGTH: 96
  - ( B ) TYPE: amino acid
  - ( C ) STRANDEDNESS: single
  - ( D ) TOPOLOGY: linear

- ( i i ) MOLECULE TYPE: amino acids

- ( i i i ) HYPOTHETICAL: irrelevant

- ( i v ) ANTI-SENSE: no

- ( v i ) ORIGINAL SOURCE:
  - ( A ) ORGANISM: Homo Sapiens
  - ( B ) INDIVIDUAL ISOLATE: 17-18 week fetus

- ( v i i ) IMMEDIATE SOURCE:
  - ( A ) LIBRARY: Stratagene cDNA Library 936206
  - ( B ) CLONE: synthesis of 4 clones

- ( x ) PUBLICATION INFORMATION:
  - ( A ) AUTHORS: Hlavin, Mary Louise
    Lemmon, Vance
  - ( B ) TITLE: Molecular structure and functional testing of human L1CAM: an interspecies comparison.
  - ( C ) JOURNAL: GENOMICS
  - ( D ) VOLUME: 11
  - ( E ) ISSUE:
  - ( F ) PAGES: 416-423

(G) DATE: 1991

(xi) SEQUENCE DESCRIPTION: SEQ ID NO: 16:

| Val | Ile | Thr | Glu | Gln | Ser | Pro | Arg | Arg | Leu | Val | Val | Phe | Pro | Thr | Asp | Asp |
|---|---|---|---|---|---|---|---|---|---|---|---|---|---|---|---|---|
| 1 | | | | 5 | | | | | 10 | | | | | 15 | | |

| Ile | Ser | Leu | Lys | Cys | Glu | Ala | Ser | Gly | Lys | Pro | Glu | Val | Gln | Phe | Arg | Trp |
|---|---|---|---|---|---|---|---|---|---|---|---|---|---|---|---|---|
| | | 20 | | | | | 25 | | | | | 30 | | | | |

| Thr | Arg | Asp | Gly | Val | His | Phe | Lys | Pro | Lys | Glu | Glu | Leu | Gly | Val | Thr | Val |
|---|---|---|---|---|---|---|---|---|---|---|---|---|---|---|---|---|
| 35 | | | | | 40 | | | | | 45 | | | | | 50 | |

| Tyr | Gln | Ser | Pro | His | Ser | Gly | Ser | Phe | Thr | Ile | Thr | Gly | Asn | Asn | Ser | Asn |
|---|---|---|---|---|---|---|---|---|---|---|---|---|---|---|---|---|
| | | | 55 | | | | | 60 | | | | | 65 | | | |

| Phe | Ala | Gln | Arg | Phe | Gln | Gly | Ile | Tyr | Arg | Cys | Phe | Ala | Ser | Asn | Lys | Leu |
|---|---|---|---|---|---|---|---|---|---|---|---|---|---|---|---|---|
| | 70 | | | | | 75 | | | | | 80 | | | | | 85 |

| Gly | Thr | Ala | Met | Ser | His | Glu | Ile | Arg | Leu | Met |
|---|---|---|---|---|---|---|---|---|---|---|
| | | | | 90 | | | | | 95 | |

(2) INFORMATION FOR SEQ ID NO:17:

(i) SEQUENCE CHARACTERISTICS:
(A) LENGTH: 106
(B) TYPE: amino acid
(C) STRANDEDNESS: single
(D) TOPOLOGY: linear (ii) MOLECULE TYPE: amino acids (iii) HYPOTHETICAL: irrelevant (iv) ANTI-SENSE: no (v) ORIGINAL SOURCE:
(A) ORGANISM: Homo Sapiens
(B) INDIVIDUAL ISOLATE: 17-18 week fetus (vii) IMMEDIATE SOURCE:
(A) LIBRARY: Stratagene cDNA Library 936206
(B) CLONE: synthesis of 4 clones (x) PUBLICATION INFORMATION:
(A) AUTHORS: Hlavin, Mary Louise
Lemmon, Vance
(B) TITLE: Molecular structure and functional
testing of human L1CAM: an interspecies
comparison.
(C) JOURNAL: GENOMICS
(D) VOLUME: 11
(E) ISSUE:
(F) PAGES: 416-423
(G) DATE: 1991

(xi) SEQUENCE DESCRIPTION: SEQ ID NO: 17:

| Ala | Glu | Gly | Ala | Pro | Lys | Trp | Pro | Lys | Glu | Thr | Val | Lys | Pro | Val | Glu | Val |
|---|---|---|---|---|---|---|---|---|---|---|---|---|---|---|---|---|
| 1 | | | | 5 | | | | | 10 | | | | | 15 | | |

| Glu | Glu | Gly | Glu | Ser | Val | Val | Leu | Pro | Cys | Asn | Pro | Pro | Pro | Ser | Ala | Glu |
|---|---|---|---|---|---|---|---|---|---|---|---|---|---|---|---|---|
| | | 20 | | | | | 25 | | | | | 30 | | | | |

| Pro | Leu | Arg | Ile | Tyr | Trp | Met | Asn | Ser | Lys | Ile | Leu | His | Ile | Lys | Gln | Asp |
|---|---|---|---|---|---|---|---|---|---|---|---|---|---|---|---|---|
| 35 | | | | | 40 | | | | | 45 | | | | | 50 | |

| Glu | Arg | Val | Thr | Met | Gly | Gln | Asn | Gly | Asn | Leu | Tyr | Phe | Ala | Asn | Val | Leu |
|---|---|---|---|---|---|---|---|---|---|---|---|---|---|---|---|---|
| | | | 55 | | | | | 60 | | | | | 65 | | | |

| Thr | Ser | Asp | Asn | His | Ser | Asp | Tyr | Ile | Cys | His | Ala | His | Phe | Pro | Gly | Thr |
|---|---|---|---|---|---|---|---|---|---|---|---|---|---|---|---|---|
| | 70 | | | | | 75 | | | | | 80 | | | | | 85 |

| Arg | Thr | Ile | Ile | Gln | Lys | Glu | Pro | Ile | Asp | Leu | Arg | Val | Lys | Ala | Thr | Asn |
|---|---|---|---|---|---|---|---|---|---|---|---|---|---|---|---|---|
| | | | | 90 | | | | | 95 | | | | | 100 | | |

| Ser | Met | Ile | Asp |
|---|---|---|---|
| | | 105 | |

( 2 ) INFORMATION FOR SEQ ID NO:18:

( i ) SEQUENCE CHARACTERISTICS:
        ( A ) LENGTH: 96
        ( B ) TYPE: amino acid
        ( C ) STRANDEDNESS: single
        ( D ) TOPOLOGY: linear ( i i ) MOLECULE TYPE: amino acids ( i i i ) HYPOTHETICAL: irrelevant ( i v ) ANTI-SENSE: no ( v i ) ORIGINAL SOURCE:
        ( A ) ORGANISM: Homo Sapiens
        ( B ) INDIVIDUAL ISOLATE: 17-18 week fetus ( v i i ) IMMEDIATE SOURCE:
        ( A ) LIBRARY: Stratagene cDNA Library 936206
        ( B ) CLONE: synthesis of 4 clones ( x ) PUBLICATION INFORMATION:
        ( A ) AUTHORS: Hlavin, Mary Louise
                  Lemmon, Vance
        ( B ) TITLE: Molecular structure and functional
               testing of human L1CAM: an interspecies
               comparison.
        ( C ) JOURNAL: GENOMICS
        ( D ) VOLUME: 11
        ( E ) ISSUE:
        ( F ) PAGES: 416-423
        ( G ) DATE: 1991

( x i ) SEQUENCE DESCRIPTION: SEQ ID NO: 18:

```
Arg  Lys  Pro  Arg  Leu  Leu  Phe  Pro  Thr  Asn  Ser  Ser  Ser  His  Leu  Val  Ala
1              5                        10                       15

Leu  Gln  Gly  Gln  Pro  Leu  Val  Leu  Glu  Cys  Ile  Ala  Glu  Gly  Phe  Pro  Thr
          20                      25                      30

Pro  Thr  Ile  Lys  Trp  Leu  Arg  Pro  Ser  Gly  Pro  Met  Pro  Ala  Asp  Arg  Val
35                      40                      45                       50

Thr  Tyr  Gln  Asn  His  Asn  Lys  Thr  Leu  Gln  Leu  Leu  Lys  Val  Gly  Glu  Glu
               55                       60                      65

Asp  Asp  Gly  Glu  Tyr  Arg  Cys  Leu  Ala  Glu  Asn  Ser  Leu  Gly  Ser  Ala  Arg
70                      75                       80                       85

His  Ala  Tyr  Tyr  Val  Thr  Val  Glu  Ala  Ala  Pro
               90                       95
```

( 2 ) INFORMATION FOR SEQ ID NO:19:

( i ) SEQUENCE CHARACTERISTICS:
        ( A ) LENGTH: 92
        ( B ) TYPE: amino acid
        ( C ) STRANDEDNESS: single
        ( D ) TOPOLOGY: linear ( i i ) MOLECULE TYPE: amino acids ( i i i ) HYPOTHETICAL: irrelevant ( i v ) ANTI-SENSE: no ( v i ) ORIGINAL SOURCE:
        ( A ) ORGANISM: Homo Sapiens
        ( B ) INDIVIDUAL ISOLATE: 17-18 week fetus ( v i i ) IMMEDIATE SOURCE:
        ( A ) LIBRARY: Stratagene cDNA Library 936206
        ( B ) CLONE: synthesis of 4 clones ( x ) PUBLICATION INFORMATION:
        ( A ) AUTHORS: Hlavin, Mary Louise Lemmon, Vance
    (B) TITLE: Molecular structure and functional
        testing of human L1CAM: an interspecies
        comparison.
    (C) JOURNAL: GENOMICS
    (D) VOLUME: 11
    (E) ISSUE:
    (F) PAGES: 416-423
    (G) DATE: 1991

(xi) SEQUENCE DESCRIPTION: SEQ ID NO: 19:

```
Tyr Trp Leu His Lys Pro Gln Ser His Leu Tyr Gly Pro Gly Glu Thr Ala
1               5                   10                  15

Arg Leu Asp Cys Gln Val Gln Gly Arg Pro Gln Pro Glu Val Thr Trp Arg
            20              25              30

Ile Asn Gly Ile Pro Val Glu Glu Leu Ala Lys Asp Gln Lys Tyr Arg Ile
35              40                  45                          50

Gln Arg Gly Ala Leu Ile Leu Ser Asn Val Gln Pro Ser Asp Thr Met Val
            55                  60              65

Thr Gln Cys Glu Ala Arg Asn Arg His Gly Leu Leu Leu Ala Asn Ala Tyr
    70              75                      80                      85

Ile Tyr Val Val Gln Leu Pro
                90
```

(2) INFORMATION FOR SEQ ID NO:20:

(i) SEQUENCE CHARACTERISTICS:
       (A) LENGTH: 93
       (B) TYPE: amino acid
       (C) STRANDEDNESS: single
       (D) TOPOLOGY: linear (ii) MOLECULE TYPE: amino acids (iii) HYPOTHETICAL: irrelevant (iv) ANTI-SENSE: no (v) ORIGINAL SOURCE:
       (A) ORGANISM: Homo Sapiens
       (B) INDIVIDUAL ISOLATE: 17-18 week fetus (vii) IMMEDIATE SOURCE:
       (A) LIBRARY: Stratagene cDNA Library 936206
       (B) CLONE: synthesis of 4 clones (x) PUBLICATION INFORMATION:
       (A) AUTHORS: Hlavin, Mary Louise
                    Lemmon, Vance
       (B) TITLE: Molecular structure and functional
           testing of human L1CAM: an interspecies
           comparison.
       (C) JOURNAL: GENOMICS
       (D) VOLUME: 11
       (E) ISSUE:
       (F) PAGES: 416-423
       (G) DATE: 1991

(xi) SEQUENCE DESCRIPTION: SEQ ID NO: 20:

```
Ala Lys Ile Leu Thr Ala Asp Asn Gln Thr Tyr Met Ala Val Gln Gly Ser
1               5                   10                  15

Thr Ala Tyr Leu Leu Cys Lys Ala Phe Gly Ala Pro Val Pro Ser Val Gln
            20              25              30

Trp Leu Asp Glu Asp Gly Thr Thr Val Leu Gln Asp Glu Arg Phe Phe Pro
35              40                  45                          50

Tyr Ala Asn Gly Thr Leu Gly Ile Arg Asp Leu Gln Ala Asn Asp Thr Gly
            55                  60              65

Arg Tyr Phe Cys Leu Ala Ala Asn Asp Gln Asn Asn Val Thr Ile Met Ala
```

```
                    70                    75                     80                     85
         Asn  Leu  Lys  Val  Lys  Asp  Ala  Thr
                               90
```

(2) INFORMATION FOR SEQ ID NO:21:

(i) SEQUENCE CHARACTERISTICS:
        (A) LENGTH: 96
        (B) TYPE: amino acid
        (C) STRANDEDNESS: single
        (D) TOPOLOGY: linear (ii) MOLECULE TYPE: amino acids (iii) HYPOTHETICAL: irrelevant (iv) ANTI-SENSE: no (vi) ORIGINAL SOURCE:
        (A) ORGANISM: Homo Sapiens
        (B) INDIVIDUAL ISOLATE: 17-18 week fetus (vii) IMMEDIATE SOURCE:
        (A) LIBRARY: Stratagene cDNA Library 936206
        (B) CLONE: synthesis of 4 clones (x) PUBLICATION INFORMATION:
        (A) AUTHORS: Hlavin, Mary Louise
                     Lemmon, Vance
        (B) TITLE: Molecular structure and functional
              testing of human L1CAM: an interspecies
              comparison.
        (C) JOURNAL: GENOMICS
        (D) VOLUME: 11
        (E) ISSUE:
        (F) PAGES: 416-423
        (G) DATE: 1991

(xi) SEQUENCE DESCRIPTION: SEQ ID NO: 21:

```
Gln  Ile  Thr  Gln  Gly  Pro  Arg  Ser  Thr  Ile  Glu  Lys  Lys  Gly  Ser  Arg  Val
 1                    5                             10                      15

Thr  Phe  Thr  Cys  Gln  Ala  Ser  Phe  Asp  Pro  Ser  Leu  Gln  Pro  Ser  Ile  Thr
               20                     25                       30

Trp  Arg  Gly  Asp  Gly  Arg  Asp  Leu  Gln  Glu  Leu  Gly  Asp  Ser  Asp  Lys  Tyr
35                        40                        45                         50

Phe  Ile  Glu  Asp  Gly  Arg  Leu  Val  Ile  His  Ser  Leu  Asp  Tyr  Ser  Asp  Gln
               55                      60                       65

Gly  Asn  Tyr  Ser  Cys  Val  Ala  Ser  Thr  Glu  Leu  Asp  Val  Val  Glu  Ser  Arg
     70                         75                      80                       85

Ala  Gln  Leu  Leu  Val  Val  Gly  Ser  Pro  Gly  Pro
                    90                    95
```

(2) INFORMATION FOR SEQ ID NO:22:

(i) SEQUENCE CHARACTERISTICS:
        (A) LENGTH: 101
        (B) TYPE: amino acid
        (C) STRANDEDNESS: single
        (D) TOPOLOGY: linear (ii) MOLECULE TYPE: amino acids (iii) HYPOTHETICAL: irrelevant (iv) ANTI-SENSE: no (vi) ORIGINAL SOURCE:
        (A) ORGANISM: Homo Sapiens
        (B) INDIVIDUAL ISOLATE: 17-18 week fetus (vii) IMMEDIATE SOURCE:

(A) LIBRARY: Stratagene cDNA Library 936206
(B) CLONE: synthesis of 4 clones (x) PUBLICATION INFORMATION:
(A) AUTHORS: Hlavin, Mary Louise
Lemmon, Vance
(B) TITLE: Molecular structure and functional
testing of human L1CAM: an interspecies
comparison.
(C) JOURNAL: GENOMICS
(D) VOLUME: 11
(E) ISSUE:
(F) PAGES: 416-423
(G) DATE: 1991

(xi) SEQUENCE DESCRIPTION: SEQ ID NO: 22:

| Val | Pro | Arg | Leu | Val | Leu | Ser | Asp | Leu | His | Leu | Leu | Thr | Gln | Ser | Gln | Val |
|---|---|---|---|---|---|---|---|---|---|---|---|---|---|---|---|---|
| 1 | | | | 5 | | | | | 10 | | | | | 15 | | |

| Arg | Val | Ser | Trp | Ser | Pro | Ala | Glu | Asp | His | Asn | Ala | Pro | Ile | Glu | Lys | Tyr |
|---|---|---|---|---|---|---|---|---|---|---|---|---|---|---|---|---|
| | | 20 | | | | | 25 | | | | | 30 | | | | |

| Asp | Ile | Glu | Phe | Glu | Asp | Lys | Glu | Met | Ala | Pro | Glu | Lys | Trp | Tyr | Ser | Leu |
|---|---|---|---|---|---|---|---|---|---|---|---|---|---|---|---|---|
| 35 | | | | | 40 | | | | | 45 | | | | | 50 | |

| Gly | Lys | Val | Pro | Gly | Asn | Gln | Thr | Ser | Thr | Thr | Leu | Lys | Leu | Ser | Pro | Tyr |
|---|---|---|---|---|---|---|---|---|---|---|---|---|---|---|---|---|
| | | | 55 | | | | | 60 | | | | | 65 | | | |

| Val | His | Tyr | Thr | Phe | Arg | Val | Thr | Ala | Ile | Asn | Lys | Tyr | Gly | Pro | Gly | Glu |
|---|---|---|---|---|---|---|---|---|---|---|---|---|---|---|---|---|
| | 70 | | | | | 75 | | | | | 80 | | | | | 85 |

| Pro | Ser | Pro | Val | Ser | Glu | Thr | Val | Val | Thr | Pro | Glu | Ala | Ala | Pro | Glu | |
|---|---|---|---|---|---|---|---|---|---|---|---|---|---|---|---|---|
| | | | | 90 | | | | | 95 | | | | | 100 | | |

(2) INFORMATION FOR SEQ ID NO:23:

(i) SEQUENCE CHARACTERISTICS:
(A) LENGTH: 96
(B) TYPE: amino acid
(C) STRANDEDNESS: single
(D) TOPOLOGY: linear (ii) MOLECULE TYPE: amino acids (iii) HYPOTHETICAL: irrelevant (iv) ANTI-SENSE: no (vi) ORIGINAL SOURCE:
(A) ORGANISM: Homo Sapiens
(B) INDIVIDUAL ISOLATE: 17-18 week fetus (vii) IMMEDIATE SOURCE:
(A) LIBRARY: Stratagene cDNA Library 936206
(B) CLONE: synthesis of 4 clones (x) PUBLICATION INFORMATION:
(A) AUTHORS: Hlavin, Mary Louise
Lemmon, Vance
(B) TITLE: Molecular structure and functional
testing of human L1CAM: an interspecies
comparison.
(C) JOURNAL: GENOMICS
(D) VOLUME: 11
(E) ISSUE:
(F) PAGES: 416-423
(G) DATE: 1991

(xi) SEQUENCE DESCRIPTION: SEQ ID NO: 23:

| Lys | Asn | Pro | Val | Asp | Val | Lys | Gly | Glu | Gly | Asn | Glu | Thr | Thr | Asn | Met | Val |
|---|---|---|---|---|---|---|---|---|---|---|---|---|---|---|---|---|
| 1 | | | | 5 | | | | | 10 | | | | | 15 | | |

| Ile | Thr | Trp | Lys | Pro | Leu | Arg | Trp | Met | Asp | Trp | Asn | Ala | Pro | Gln | Val | Gln |
|---|---|---|---|---|---|---|---|---|---|---|---|---|---|---|---|---|
| | | 20 | | | | | 25 | | | | | 30 | | | | |

| Tyr | Arg | Val | Gln | Trp | Arg | Pro | Gln | Gly | Thr | Arg | Gly | Pro | Trp | Gln | Glu | Gln |
|---|---|---|---|---|---|---|---|---|---|---|---|---|---|---|---|---|
| 35 | | | | | 40 | | | | | 45 | | | | | 50 | |

```
            Ile  Val  Ser  Asp  Pro  Phe  Leu  Val  Val  Ser  Asn  Thr  Ser  Thr  Phe  Val  Pro
                           5 5                      6 0                     6 5

Tyr  Glu  Ile  Lys  Val  Gln  Ala  Val  Asn  Ser  Gln  Gly  Lys  Gly  Pro  Glu  Pro
                 7 0                      7 5                     8 0                          8 5

Gln  Val  Thr  Ile  Gly  Tyr  Ser  Gly  Glu  Asp  Tyr
                                 9 0                     9 5
```

( 2 ) INFORMATION FOR SEQ ID NO:24:

( i ) SEQUENCE CHARACTERISTICS:
        ( A ) LENGTH: 106
        ( B ) TYPE: amino acid
        ( C ) STRANDEDNESS: single
        ( D ) TOPOLOGY: linear ( i i ) MOLECULE TYPE: amino acids ( i i i ) HYPOTHETICAL: irrelevant ( i v ) ANTI-SENSE: no ( v i ) ORIGINAL SOURCE:
        ( A ) ORGANISM: Homo Sapiens
        ( B ) INDIVIDUAL ISOLATE: 17-18 week fetus ( v i i ) IMMEDIATE SOURCE:
        ( A ) LIBRARY: Stratagene cDNA Library 936206
        ( B ) CLONE: synthesis of 4 clones ( x ) PUBLICATION INFORMATION:
        ( A ) AUTHORS: Hlavin, Mary Louise
                Lemmon, Vance
        ( B ) TITLE: Molecular structure and functional
              testing of human L1CAM: an interspecies
              comparison.
        ( C ) JOURNAL: GENOMICS
        ( D ) VOLUME: 11
        ( E ) ISSUE:
        ( F ) PAGES: 416-423
        ( G ) DATE: 1991

( x i ) SEQUENCE DESCRIPTION: SEQ ID NO: 24:

```
            Pro  Gln  Ala  Ile  Pro  Glu  Leu  Glu  Gly  Ile  Glu  Ile  Leu  Asn  Ser  Ser  Ala
            1                    5                      1 0                     1 5

Val  Leu  Val  Lys  Trp  Arg  Pro  Val  Asp  Leu  Ala  Gln  Val  Lys  Gly  His  Leu
                      2 0                      2 5                     3 0

Arg  Gly  Tyr  Asn  Val  Thr  Tyr  Trp  Arg  Glu  Gly  Ser  Gln  Arg  Lys  His  Ser
            3 5                            4 0                     4 5                          5 0

Lys  Arg  His  Ile  His  Lys  Asp  His  Val  Val  Val  Pro  Ala  Asn  Thr  Thr  Ser
                           5 5                      6 0                     6 5

Val  Ile  Leu  Ser  Gly  Leu  Arg  Pro  Tyr  Ser  Ser  Tyr  His  Leu  Glu  Val  Gln
                 7 0                      7 5                     8 0                          8 5

Ala  Phe  Asn  Gly  Arg  Gly  Ser  Gly  Pro  Ala  Ser  Glu  Phe  Thr  Phe  Ser  Thr
                                 9 0                     9 5                     1 0 0

Pro  Glu  Gly  Val
                      1 0 5
```

( 2 ) INFORMATION FOR SEQ ID NO:25:

( i ) SEQUENCE CHARACTERISTICS:
        ( A ) LENGTH: 97
        ( B ) TYPE: amino acid
        ( C ) STRANDEDNESS: single
        ( D ) TOPOLOGY: linear ( i i ) MOLECULE TYPE: amino acids ( i i i ) HYPOTHETICAL: irrelevant (iv) ANTI-SENSE: no (vi) ORIGINAL SOURCE:
 (A) ORGANISM: Homo Sapiens
 (B) INDIVIDUAL ISOLATE: 17-18 week fetus (vii) IMMEDIATE SOURCE:
 (A) LIBRARY: Stratagene cDNA Library 936206
 (B) CLONE: synthesis of 4 clones (x) PUBLICATION INFORMATION:
 (A) AUTHORS: Hlavin, Mary Louise
  Lemmon, Vance
 (B) TITLE: Molecular structure and functional
  testing of human L1CAM: an interspecies
  comparison.
 (C) JOURNAL: GENOMICS
 (D) VOLUME: 11
 (E) ISSUE:
 (F) PAGES: 416-423
 (G) DATE: 1991

(xi) SEQUENCE DESCRIPTION: SEQ ID NO: 25:

```
Pro  Gly  His  Pro  Glu  Ala  Leu  His  Leu  Glu  Cys  Gln  Ser  Asn  Thr  Ser  Leu
1               5                        10                      15

Leu  Leu  Arg  Trp  Gln  Pro  Pro  Leu  Ser  His  Asn  Gly  Val  Leu  Thr  Gly  Tyr
         20                   25                      30

Val  Leu  Ser  Tyr  His  Pro  Leu  Asp  Glu  Gly  Gly  Lys  Gly  Gln  Leu  Ser  Phe
35                        40                      45                            50

Asn  Leu  Arg  Asp  Pro  Glu  Leu  Arg  Thr  His  Asn  Leu  Thr  Asp  Leu  Ser  Pro
              55                        60                      65

His  Leu  Arg  Tyr  Arg  Phe  Gln  Leu  Gln  Ala  Thr  Thr  Lys  Glu  Gly  Pro  Gly
     70                        75                 80                           85

Glu  Ala  Ile  Val  Arg  Glu  Gly  Gly  Thr  Met  Ala  Leu
                    90                   95
```

(2) INFORMATION FOR SEQ ID NO:26:

(i) SEQUENCE CHARACTERISTICS:
  (A) LENGTH: 99
  (B) TYPE: amino acid
  (C) STRANDEDNESS: single
  (D) TOPOLOGY: linear (ii) MOLECULE TYPE: amino acids (iii) HYPOTHETICAL: irrelevant (iv) ANTI-SENSE: no (vi) ORIGINAL SOURCE:
  (A) ORGANISM: Homo Sapiens
  (B) INDIVIDUAL ISOLATE: 17-18 week fetus (vii) IMMEDIATE SOURCE:
  (A) LIBRARY: Stratagene cDNA Library 936206
  (B) CLONE: synthesis of 4 clones (x) PUBLICATION INFORMATION:
  (A) AUTHORS: Hlavin, Mary Louise
   Lemmon, Vance
  (B) TITLE: Molecular structure and functional
   testing of human L1CAM: an interspecies
   comparison.
  (C) JOURNAL: GENOMICS
  (D) VOLUME: 11
  (E) ISSUE:
  (F) PAGES: 416-423
  (G) DATE: 1991

(xi) SEQUENCE DESCRIPTION: SEQ ID NO: 26:

| | | | | | | | | | | | | | | |
|---|---|---|---|---|---|---|---|---|---|---|---|---|---|---|
| Ser 1 | Gly | Ile | Ser | Asp 5 | Phe | Gly | Asn | Ile | Ser 10 | Ala | Thr | Ala | Gly | Glu Asn Tyr 15 |
| Ser | Val | Val 20 | Ser | Trp | Val | Pro | Lys 25 | Glu | Gly | Gln | Cys | Asn 30 | Phe | Arg Phe His |
| Ile 35 | Leu | Phe | Lys | Ala | Leu 40 | Gly | Glu | Glu | Lys | Gly 45 | Gly | Ala | Ser | Leu Ser Pro 50 |
| Gln | Tyr | Val | Ser 55 | Tyr | Asn | Gln | Ser | Ser 60 | Tyr | Thr | Gln | Trp | Asp 65 | Leu Gln Pro |
| Asp | Thr 70 | Asp | Tyr | Glu | Ile | His 75 | Leu | Phe | Lys | Glu | Arg 80 | Met | Phe | Arg His Gln 85 |
| Met | Ala | Val | Lys | Thr 90 | Asn | Gly | Thr | Gly | Arg 95 | Val | Arg | Leu | Pro | |

( 2 ) INFORMATION FOR SEQ ID NO: 27:

( i ) SEQUENCE CHARACTERISTICS:
        ( A ) LENGTH: 144
        ( B ) TYPE: amino acid
        ( C ) STRANDEDNESS: single
        ( D ) TOPOLOGY: linear ( i i ) MOLECULE TYPE: amino acids ( i i i ) HYPOTHETICAL: irrelevant ( i v ) ANTI-SENSE: no ( v i ) ORIGINAL SOURCE:
        ( A ) ORGANISM: Homo Sapiens
        ( B ) INDIVIDUAL ISOLATE: 17-18 week fetus ( v i i ) IMMEDIATE SOURCE:
        ( A ) LIBRARY: Stratagene cDNA Library 936206
        ( B ) CLONE: synthesis of 4 clones ( x ) PUBLICATION INFORMATION:
        ( A ) AUTHORS: Hlavin, Mary Louise
                      Lemmon, Vance
        ( B ) TITLE: Molecular structure and functional
               testing of human L1CAM: an interspecies
               comparison.
        ( C ) JOURNAL: GENOMICS
        ( D ) VOLUME: 11
        ( E ) ISSUE:
        ( F ) PAGES: 416-423
        ( G ) DATE: 1991

( x i ) SEQUENCE DESCRIPTION: SEQ ID NO: 27:

| | | | | | | | | | | | | | | |
|---|---|---|---|---|---|---|---|---|---|---|---|---|---|---|
| Pro 1 | Ala | Gly | Phe | Ala 5 | Thr | Glu | Gly | Trp | Phe 10 | Ile | Gly | Phe | Val | Ser Ala Ile 15 |
| Ile | Leu | Leu 20 | Leu | Leu | Val | Leu | Leu 25 | Ile | Leu | Cys | Phe | Ile 30 | Lys | Arg Ser Lys |
| Gly 35 | Gly | Lys | Tyr | Ser | Val 40 | Lys | Asp | Lys | Glu | Asp 45 | Thr | Gln | Val | Asp Ser Glu 50 |
| Ala | Arg | Pro | Met 55 | Lys | Asp | Glu | Thr | Phe 60 | Gly | Glu | Tyr | Arg | Ser 65 | Leu Glu Ser |
| Asp | Asn 70 | Glu | Glu | Lys | Ala | Phe 75 | Gly | Ser | Ser | Gln | Pro 80 | Ser | Leu | Asn Gly Asp 85 |
| Ile | Lys | Pro | Leu | Gly 90 | Ser | Asp | Asp | Ser 95 | Leu | Ala | Asp | Tyr 100 | Gly | Gly Ser Val |
| Asp 105 | Val | Gln | Phe | Asn | Glu 110 | Asp | Gly | Ser | Phe | Ile 115 | Gly | Gln | Tyr | Ser Gly Lys |
| Lys 120 | Glu | Lys | Glu | Ala | Ala 125 | Gly | Gly | Asn | Asp | Ser 130 | Ser | Gly | Ala | Thr Ser Pro 135 |
| Ile | Asn | Pro | Ala | Val | Ala | Leu | Glu | | | | | | | |

140

(2) INFORMATION FOR SEQ ID NO:28:

(i) SEQUENCE CHARACTERISTICS:
        (A) LENGTH: 90
        (B) TYPE: amino acid
        (C) STRANDEDNESS: single
        (D) TOPOLOGY: linear (ii) MOLECULE TYPE: amino acids (iii) HYPOTHETICAL: irrelevant (iv) ANTI-SENSE: no (vi) ORIGINAL SOURCE:
        (A) ORGANISM: CHICKEN
        (B) INDIVIDUAL ISOLATE: e9-e14 embryos brains, adult brains (vii) IMMEDIATE SOURCE:
        (A) LIBRARY: many lambda GT11 cDNA and genomic libraries
        (B) CLONE: synthesis of 14 clones (x) PUBLICATION INFORMATION:
        (A) AUTHORS: Burgoon, M.P.
                 Grumet, M.
                 Mauro, V.
                 Edelman, G.M.
                 Cunningham, B.A.
        (B) TITLE: Structure of the chicken neuron-
              glial cell adhesion molecule, Ng-CAM:
              Origin of the polypeptides and
              relation to the Ig superfamily.
        (C) JOURNAL: J. Cell Biol.
        (D) VOLUME: 112
        (E) ISSUE:
        (F) PAGES: 1017-1029
        (G) DATE: 1991

(xi) SEQUENCE DESCRIPTION: SEQ ID NO: 28:

```
Glu Leu Thr Glu Glu Pro Pro Glu Gln Leu Val Val Phe Pro Ser Asp Asp
1               5                   10                  15
Ile Val Leu Lys Cys Val Ala Thr Gly Asn Pro Pro Val Gln Tyr Arg Trp
        20              25                  30
Ser Arg Glu Ile Ser Pro Ser Ser Pro Arg Ser Thr Gly Gly Ser Arg Trp
35                  40                  45                  50
Ser Pro Asp Arg His Leu Val Ile Asn Ala Thr Leu Ala Ala Arg Leu Gln
            55                  60                  65
Gly Arg Phe Arg Cys Phe Ala Thr Asn Ala Leu Gly Thr Ala Val Ser Pro
    70                  75                  80                  85
Glu Ala Asn Val Ile
                90
```

(2) INFORMATION FOR SEQ ID NO:29:

(i) SEQUENCE CHARACTERISTICS:
        (A) LENGTH: 106
        (B) TYPE: amino acid
        (C) STRANDEDNESS: single
        (D) TOPOLOGY: linear (ii) MOLECULE TYPE: amino acids (iii) HYPOTHETICAL: irrelevant (iv) ANTI-SENSE: no (vi) ORIGINAL SOURCE:
        (A) ORGANISM: CHICKEN
        (B) INDIVIDUAL ISOLATE: e9-e14 embryos brains, adult brains (vii) IMMEDIATE SOURCE:
    (A) LIBRARY: many lambda GT11 cDNA and genomic libraries
    (B) CLONE: synthesis of 14 clones (x) PUBLICATION INFORMATION:
    (A) AUTHORS: Burgoon, M.P.
                 Grumet, M.
                 Mauro, V.
                 Edelman, G.M.
                 Cunningham, B.A.
    (B) TITLE: Structure of the chicken neuron-
               glial cell adhesion molecule, Ng-CAM:
               Origin of the polypeptides and
               relation to the Ig superfamily.
    (C) JOURNAL: J. Cell Biol.
    (D) VOLUME: 112
    (E) ISSUE:
    (F) PAGES: 1017-1029
    (G) DATE: 1991

(xi) SEQUENCE DESCRIPTION: SEQ ID NO: 29:

```
Ala Glu Asn Thr Pro Gln Trp Pro Lys Lys Lys Val Thr Pro Val Glu Val
 1               5                   10                  15
Glu Glu Gly Asp Pro Val Val Leu Pro Cys Asp Pro Pro Glu Ser Ala Val
        20              25                  30
Pro Pro Lys Ile Tyr Trp Leu Asn Ser Asp Ile Val His Ile Ala Gln Asp
 35              40                  45                  50
Glu Arg Val Ser Met Gly Gln Asp Gly Asn Leu Tyr Phe Ser Asn Ala Met
            55              60                  65
Val Gly Asp Ser His Pro Asp Tyr Ile Cys His Ala His Phe Leu Gly Pro
    70              75                  80                  85
Arg Thr Ile Ile Gln Lys Glu Pro Leu Asp Leu Arg Val Ala Pro Ser Asn
                90              95                  100
Ala Val Arg Ser
            105
```

(2) INFORMATION FOR SEQ ID NO: 30:

(i) SEQUENCE CHARACTERISTICS:
        (A) LENGTH: 94
        (B) TYPE: amino acid
        (C) STRANDEDNESS: single
        (D) TOPOLOGY: linear (ii) MOLECULE TYPE: amino acids (iii) HYPOTHETICAL: irrelevant (iv) ANTI-SENSE: no (v) ORIGINAL SOURCE:
        (A) ORGANISM: CHICKEN
        (B) INDIVIDUAL ISOLATE: e9-e14 embryos brains, adult brains (vii) IMMEDIATE SOURCE:
        (A) LIBRARY: many lambda GT11 cDNA and genomic libraries
        (B) CLONE: synthesis of 14 clones (x) PUBLICATION INFORMATION:
        (A) AUTHORS: Burgoon, M.P.
                     Grumet, M.
                     Mauro, V.
                     Edelman, G.M.
                     Cunningham, B.A.
        (B) TITLE: Structure of the chicken neuron-
                   glial cell adhesion molecule, Ng-CAM:
                   Origin of the polypeptides and
                   relation to the Ig superfamily.
        (C) JOURNAL: J. Cell Biol.
        (D) VOLUME: 112
        (E) ISSUE:
        (F) PAGES: 1017-1029

(G) DATE: 1991

(xi) SEQUENCE DESCRIPTION: SEQ ID NO: 30:

| Arg | Arg | Pro | Arg | Leu | Leu | Leu | Pro | Arg | Asp | Pro | Gln | Thr | Thr | Thr | Ile | Ala |
|---|---|---|---|---|---|---|---|---|---|---|---|---|---|---|---|---|
| 1 | | | | 5 | | | | | 10 | | | | | 15 | | |
| Leu | Arg | Gly | Gly | Ser | Val | Val | Leu | Glu | Cys | Ile | Ala | Glu | Gly | Leu | Pro | Thr |
| | | 20 | | | | | 25 | | | | | 30 | | | | |
| Pro | Trp | Val | Arg | Trp | Arg | Arg | Leu | Asn | Gly | Pro | Leu | Leu | Pro | Gly | Gly | Val |
| 35 | | | | | 40 | | | | | 45 | | | | | | 50 |
| Gly | Asn | Phe | Asn | Lys | Thr | Leu | Arg | Leu | Trp | Gly | Val | Thr | Glu | Ser | Asp | Asp |
| | | | 55 | | | | | 60 | | | | | 65 | | | |
| Gly | Glu | Tyr | Glu | Cys | Val | Ala | Glu | Asn | Gly | Arg | Gly | Thr | Ala | Arg | Gly | Thr |
| | 70 | | | | | 75 | | | | | 80 | | | | | 85 |
| His | Ser | Val | Thr | Val | Glu | Ala | Ala | Pro | | | | | | | | |
| | | | | 90 | | | | | | | | | | | | |

(2) INFORMATION FOR SEQ ID NO:31:

(i) SEQUENCE CHARACTERISTICS:
        (A) LENGTH: 91
        (B) TYPE: amino acid
        (C) STRANDEDNESS: single
        (D) TOPOLOGY: linear (ii) MOLECULE TYPE: amino acids (iii) HYPOTHETICAL: irrelevant (iv) ANTI-SENSE: no (v) ORIGINAL SOURCE:
        (A) ORGANISM: CHICKEN
        (B) INDIVIDUAL ISOLATE: e9-e14 embryos brains, adult brains (vii) IMMEDIATE SOURCE:
        (A) LIBRARY: many lambda GT11 cDNA and genomic libraries
        (B) CLONE: synthesis of 14 clones (x) PUBLICATION INFORMATION:
        (A) AUTHORS: Burgoon, M.P.
                Grumet, M.
                Mauro, V.
                Edelman, G.M.
                Cunningham, B.A.
        (B) TITLE: Structure of the chicken neuron-
                glial cell adhesion molecule, Ng-CAM:
                Origin of the polypeptides and
                relation to the Ig superfamily.
        (C) JOURNAL: J. Cell Biol.
        (D) VOLUME: 112
        (E) ISSUE:
        (F) PAGES: 1017-1029
        (G) DATE: 1991

(xi) SEQUENCE DESCRIPTION: SEQ ID NO: 31:

| Tyr | Trp | Val | Arg | Arg | Pro | Gln | Ser | Gly | Val | Phe | Gly | Pro | Gly | Glu | Thr | Ala |
|---|---|---|---|---|---|---|---|---|---|---|---|---|---|---|---|---|
| 1 | | | | 5 | | | | | 10 | | | | | 15 | | |
| Arg | Leu | Asp | Cys | Glu | Val | Gly | Gly | Lys | Pro | Arg | Pro | Gln | Ile | Gln | Trp | Ser |
| | | 20 | | | | | 25 | | | | | 30 | | | | |
| Ile | Asn | Gly | Val | Pro | Ile | Glu | Ala | Ala | Gly | Ala | Glu | Arg | Arg | Trp | Leu | Arg |
| 35 | | | | | 40 | | | | | 45 | | | | | 50 | |
| Gly | Gly | Ala | Leu | Val | Leu | Pro | Glu | Leu | Arg | Pro | Asn | Asp | Ser | Ala | Val | Leu |
| | | | 55 | | | | | 60 | | | | | 65 | | | |
| Gln | Cys | Glu | Ala | Arg | Asn | Arg | His | Gly | Pro | Leu | Leu | Ala | Asn | Ala | Phe | Leu |
| | 70 | | | | | 75 | | | | | 80 | | | | | 85 |
| His | Val | Val | Glu | Leu | Pro | | | | | | | | | | | |
| | | | | 90 | | | | | | | | | | | | |

(2) INFORMATION FOR SEQ ID NO:32:

(i) SEQUENCE CHARACTERISTICS:
        (A) LENGTH: 93
        (B) TYPE: amino acid
        (C) STRANDEDNESS: single
        (D) TOPOLOGY: linear (ii) MOLECULE TYPE: amino acids (iii) HYPOTHETICAL: irrelevant (iv) ANTI-SENSE: no (vi) ORIGINAL SOURCE:
        (A) ORGANISM: CHICKEN
        (B) INDIVIDUAL ISOLATE: e9-e14 embryos brains, adult brains (vii) IMMEDIATE SOURCE:
        (A) LIBRARY: many lambda GT11 cDNA and genomic libraries
        (B) CLONE: synthesis of 14 clones (x) PUBLICATION INFORMATION:
        (A) AUTHORS: Burgoon, M.P.
                Grumet, M.
                Mauro, V.
                Edelman, G.M.
                Cunningham, B.A.
        (B) TITLE: Structure of the chicken neuron-
               glial cell adhesion molecule, Ng-CAM:
               Origin of the polypeptides and
               relation to the Ig superfamily.
        (C) JOURNAL: J. Cell Biol.
        (D) VOLUME: 112
        (E) ISSUE:
        (F) PAGES: 1017-1029
        (G) DATE: 1991

(xi) SEQUENCE DESCRIPTION: SEQ ID NO: 32:

```
Leu  Arg  Met  Leu  Thr  Ala  Asp  Glu  Gln  Arg  Tyr  Glu  Val  Val  Glu  Asn  Gln
1                   5                        10                      15

Thr  Val  Phe  Leu  His  Cys  Arg  Thr  Phe  Gly  Ala  Pro  Ala  Pro  Asn  Val  Glu
          20                       25                      30

Trp  Leu  Thr  Pro  Thr  Leu  Glu  Pro  Ala  Leu  Gln  Asp  Asp  Arg  Ser  Phe  Val
35                       40                       45                           50

Phe  Thr  Asn  Gly  Ser  Leu  Arg  Val  Ser  Ala  Val  Arg  Gly  Gly  Asp  Gly  Gly
               55                       60                       65

Val  Tyr  Thr  Cys  Met  Ala  Gln  Asn  Ala  His  Ser  Asn  Gly  Ser  Leu  Thr  Ala
     70                       75                       80                           85

Leu  Leu  Glu  Val  Arg  Ala  Pro  Thr
                    90
```

(2) INFORMATION FOR SEQ ID NO:33:

(i) SEQUENCE CHARACTERISTICS:
        (A) LENGTH: 92
        (B) TYPE: amino acid
        (C) STRANDEDNESS: single
        (D) TOPOLOGY: linear (ii) MOLECULE TYPE: amino acids (iii) HYPOTHETICAL: irrelevant (iv) ANTI-SENSE: no (vi) ORIGINAL SOURCE:
        (A) ORGANISM: CHICKEN
        (B) INDIVIDUAL ISOLATE: e9-e14 embryos brains, adult brains (vii) IMMEDIATE SOURCE:

(A) LIBRARY: many lambda GT11 cDNA and genomic libraries
(B) CLONE: synthesis of 14 clones (x) PUBLICATION INFORMATION:
(A) AUTHORS: Burgoon, M.P.
Grumet, M.
Mauro, V.
Edelman, G.M.
Cunningham, B.A.
(B) TITLE: Structure of the chicken neuron-
glial cell adhesion molecule, Ng-CAM:
Origin of the polypeptides and
relation to the Ig superfamily.
(C) JOURNAL: J. Cell Biol.
(D) VOLUME: 112
(E) ISSUE:
(F) PAGES: 1017-1029
(G) DATE: 1991

(xi) SEQUENCE DESCRIPTION: SEQ ID NO: 33:

```
Arg Ile Ser Ala Pro Pro Arg Ser Ala Thr Ala Lys Lys Gly Glu Thr Val
1               5                   10                  15
Thr Phe His Cys Gly Ala Thr Phe Asp Pro Ala Val Thr Pro Gly Glu Leu
        20                  25                  30
Arg Trp Leu Arg Gly Gly Gln Pro Leu Pro Asp Asp Pro Arg Tyr Ser Val
35                      40                  45                      50
Ala Ala Glu Met Thr Val Ser Asn Val Asp Tyr Gly Asp Glu Gly Thr Ile
                55                  60                  65
Gln Cys Arg Ala Ser Thr Pro Leu Asp Ser Ala Glu Ala Glu Ala Gln Leu
        70                  75                  80                      85
Arg Val Val Gly Arg Pro Pro
                90
```

(2) INFORMATION FOR SEQ ID NO:34:

(i) SEQUENCE CHARACTERISTICS:
(A) LENGTH: 98
(B) TYPE: amino acid
(C) STRANDEDNESS: single
(D) TOPOLOGY: linear (ii) MOLECULE TYPE: amino acids (iii) HYPOTHETICAL: irrelevant (iv) ANTI-SENSE: no (v) ORIGINAL SOURCE:
(A) ORGANISM: CHICKEN
(B) INDIVIDUAL ISOLATE: e9-e14 embryos brains, adult brains (vii) IMMEDIATE SOURCE:
(A) LIBRARY: many lambda GT11 cDNA and genomic libraries
(B) CLONE: synthesis of 14 clones (x) PUBLICATION INFORMATION:
(A) AUTHORS: Burgoon, M.P.
Grumet, M.
Mauro, V.
Edelman, G.M.
Cunningham, B.A.
(B) TITLE: Structure of the chicken neuron-
glial cell adhesion molecule, Ng-CAM:
Origin of the polypeptides and
relation to the Ig superfamily.
(C) JOURNAL: J. Cell Biol.
(D) VOLUME: 112
(E) ISSUE:
(F) PAGES: 1017-1029
(G) DATE: 1991

(xi) SEQUENCE DESCRIPTION: SEQ ID NO: 34:

-continued

| | | | | | | | | | | | | | | | |
|---|---|---|---|---|---|---|---|---|---|---|---|---|---|---|---|
| Ser | Arg | Asp | Leu | Gln | Val | Met | Glu | Val | Asp | Glu | His | Arg | Val | Arg | Leu | Ser |
| 1 | | | | 5 | | | | | 10 | | | | | 15 | | |
| Trp | Thr | Pro | Gly | Asp | Asp | His | Asn | Ser | Pro | Ile | Glu | Lys | Phe | Val | Val | Glu |
| | | 20 | | | | | 25 | | | | | 30 | | | | |
| Glu | Glu | Glu | Glu | Arg | Glu | Asp | Leu | Gln | Arg | Gly | Phe | Gly | Ala | Ala | Asp | Val |
| 35 | | | | | 40 | | | | | 45 | | | | | 50 | |
| Pro | Gly | Gln | Pro | Trp | Thr | Pro | Pro | Leu | Pro | Leu | Ser | Pro | Tyr | Gly | Arg | Phe |
| | | | 55 | | | | | 60 | | | | | 65 | | | |
| Pro | Phe | Arg | Val | Val | Ala | Val | Asn | Ala | Tyr | Gly | Arg | Gly | Glu | His | His | Ala |
| | | 70 | | | | 75 | | | | | 80 | | | | | 85 |
| Pro | Ser | Ala | Pro | Ile | Glu | Thr | Pro | Pro | Ala | Ala | Pro | Glu | | | | |
| | | | | 90 | | | | | 95 | | | | | | | |

(2) INFORMATION FOR SEQ ID NO:35:

(i) SEQUENCE CHARACTERISTICS:
        (A) LENGTH: 104
        (B) TYPE: amino acid
        (C) STRANDEDNESS: single
        (D) TOPOLOGY: linear (ii) MOLECULE TYPE: amino acids (iii) HYPOTHETICAL: irrelevant (iv) ANTI-SENSE: no (v) ORIGINAL SOURCE:
        (A) ORGANISM: CHICKEN
        (B) INDIVIDUAL ISOLATE: e9-e14 embryos brains, adult brains (vii) IMMEDIATE SOURCE:
        (A) LIBRARY: many lambda GT11 cDNA and genomic libraries
        (B) CLONE: synthesis of 14 clones (x) PUBLICATION INFORMATION:
        (A) AUTHORS: Burgoon, M.P.
                Grumet, M.
                Mauro, V.
                Edelman, G.M.
                Cunningham, B.A.
        (B) TITLE: Structure of the chicken neuron-
                glial cell adhesion molecule, Ng-CAM:
                Origin of the polypeptides and
                relation to the Ig superfamily.
        (C) JOURNAL: J. Cell Biol.
        (D) VOLUME: 112
        (E) ISSUE:
        (F) PAGES: 1017-1029
        (G) DATE: 1991

(xi) SEQUENCE DESCRIPTION: SEQ ID NO: 35:

| | | | | | | | | | | | | | | | |
|---|---|---|---|---|---|---|---|---|---|---|---|---|---|---|---|
| Arg | Asn | Pro | Gly | Gly | Val | His | Gly | Glu | Gly | Asn | Glu | Thr | Gly | Asn | Leu | Val |
| 1 | | | | 5 | | | | | 10 | | | | | 15 | | |
| Ile | Thr | Trp | Glu | Pro | Leu | Pro | Pro | Gln | Ala | Trp | Asn | Ala | Pro | Trp | Ala | Arg |
| | | 20 | | | | | 25 | | | | | 30 | | | | |
| Tyr | Arg | Val | Gln | Trp | Arg | Pro | Leu | Glu | Glu | Pro | Gly | Gly | Gly | Gly | Pro | Ser |
| 35 | | | | | 40 | | | | | 45 | | | | | 50 | |
| Gly | Gly | Phe | Pro | Trp | Ala | Glu | Ser | Thr | Val | Asp | Ala | Pro | Pro | Val | Val | Val |
| | | | 55 | | | | | 60 | | | | | 65 | | | |
| Gly | Gly | Leu | Pro | Pro | Phe | Ser | Pro | Phe | Gln | Ile | Arg | Val | Gln | Ala | Val | Asn |
| | | 70 | | | | 75 | | | | | 80 | | | | | 85 |
| Gly | Ala | Gly | Lys | Gly | Pro | Glu | Ala | Thr | Pro | Gly | Val | Gly | His | Ser | Gly | Glu |
| | | | | 90 | | | | | 95 | | | | | 100 | | |
| Asp | Leu | | | | | | | | | | | | | | | |

( 2 ) INFORMATION FOR SEQ ID NO:36:

( i ) SEQUENCE CHARACTERISTICS:
        ( A ) LENGTH: 126
        ( B ) TYPE: amino acid
        ( C ) STRANDEDNESS: single
        ( D ) TOPOLOGY: linear ( i i ) MOLECULE TYPE: amino acids ( i i i ) HYPOTHETICAL: irrelevant ( i v ) ANTI-SENSE: no ( v i ) ORIGINAL SOURCE:
        ( A ) ORGANISM: CHICKEN
        ( B ) INDIVIDUAL ISOLATE: e9-e14 embryos brains, adult brains ( v i i ) IMMEDIATE SOURCE:
        ( A ) LIBRARY: many lambda GT11 cDNA and genomic libraries
        ( B ) CLONE: synthesis of 14 clones ( x ) PUBLICATION INFORMATION:
        ( A ) AUTHORS: Burgoon, M.P.
            Grumet, M.
            Mauro, V.
            Edelman, G.M.
            Cunningham, B.A.
        ( B ) TITLE: Structure of the chicken neuron-
            glial cell adhesion molecule, Ng-CAM:
            Origin of the polypeptides and
            relation to the Ig superfamily.
        ( C ) JOURNAL: J. Cell Biol.
        ( D ) VOLUME: 112
        ( E ) ISSUE:
        ( F ) PAGES: 1017-1029
        ( G ) DATE: 1991

( x i ) SEQUENCE DESCRIPTION: SEQ ID NO: 36:

```
Pro  Leu  Val  Tyr  Pro  Glu  Asn  Val  Gly  Val  Glu  Leu  Leu  Asn  Ser  Ser  Thr
1              5                        10                       15

Val  Arg  Val  Arg  Trp  Thr  Leu  Gly  Gly  Gly  Pro  Lys  Glu  Leu  Arg  Gly  Arg
          20                       25                  30

Leu  Arg  Gly  Phe  Arg  Val  Leu  Tyr  Trp  Arg  Leu  Gly  Trp  Val  Gly  Glu  Arg
35                       40                       45                       50

Ser  Arg  Arg  Gln  Ala  Pro  Pro  Asp  Pro  Pro  Gln  Ile  Pro  Gln  Ser  Pro  Ala
               55                      60                       65

Glu  Asp  Pro  Pro  Pro  Phe  Pro  Pro  Val  Ala  Leu  Thr  Val  Gly  Gly  Asp  Ala
     70                       75                  80                            85

Arg  Gly  Ala  Leu  Leu  Gly  Gly  Leu  Arg  Pro  Trp  Ser  Arg  Tyr  Gln  Leu  Arg
                    90                  95                            100

Val  Leu  Val  Phe  Asn  Gly  Arg  Gly  Asp  Gly  Pro  Pro  Ser  Glu  Pro  Ile  Ala
               105                      110                 115

Phe  Glu  Thr  Pro  Glu  Gly  Val
120                      125
```

( 2 ) INFORMATION FOR SEQ ID NO:37:

( i ) SEQUENCE CHARACTERISTICS:
        ( A ) LENGTH: 98
        ( B ) TYPE: amino acid
        ( C ) STRANDEDNESS: single
        ( D ) TOPOLOGY: linear ( i i ) MOLECULE TYPE: amino acids ( i i i ) HYPOTHETICAL: irrelevant ( i v ) ANTI-SENSE: no ( v i ) ORIGINAL SOURCE:

(A) ORGANISM: CHICKEN
                (B) INDIVIDUAL ISOLATE: e9-e14 embryos brains, adult brains (vii) IMMEDIATE SOURCE:
                (A) LIBRARY: many lambda GT11 cDNA and genomic libraries
                (B) CLONE: synthesis of 14 clones (x) PUBLICATION INFORMATION:
                (A) AUTHORS: Burgoon, M.P.
                        Grumet, M.
                        Mauro, V.
                        Edelman, G.M.
                        Cunningham, B.A.
                (B) TITLE: Structure of the chicken neuron-
                        glial cell adhesion molecule, Ng-CAM:
                        Origin of the polypeptides and
                        relation to the Ig superfamily.
                (C) JOURNAL: J. Cell Biol.
                (D) VOLUME: 112
                (E) ISSUE:
                (F) PAGES: 1017-1029
                (G) DATE: 1991

(xi) SEQUENCE DESCRIPTION: SEQ ID NO: 37:

Pro Gly Pro Pro Glu Glu Leu Arg Val Glu Arg Leu Asp Asp Thr Ala Leu
1               5                   10                  15

Ser Val Val Glu Arg Arg Thr Phe Lys Arg Ser Ile Thr Gly Tyr Val Leu
        20                  25                  30

Arg Tyr Gln Gln Val Glu Pro Gly Ser Ala Leu Pro Gly Gly Ser Val Leu
35                  40                  45                  50

Arg Asp Pro Gln Cys Asp Leu Arg Gly Leu Asn Ala Arg Ser Arg Tyr Arg
            55                  60                  65

Leu Ala Leu Pro Ser Thr Pro Arg Glu Arg Pro Ala Leu Gln Thr Val Gly
        70              75              80                      85

Ser Thr Lys Pro Glu Pro Pro Ser Pro Leu Trp Ser Arg
                90                  95

(2) INFORMATION FOR SEQ ID NO:38:

(i) SEQUENCE CHARACTERISTICS:
                (A) LENGTH: 93
                (B) TYPE: amino acid
                (C) STRANDEDNESS: single
                (D) TOPOLOGY: linear (ii) MOLECULE TYPE: amino acids (iii) HYPOTHETICAL: irrelevant (iv) ANTI-SENSE: no (v) ORIGINAL SOURCE:
                (A) ORGANISM: CHICKEN
                (B) INDIVIDUAL ISOLATE: e9-e14 embryos brains, adult brains (vii) IMMEDIATE SOURCE:
                (A) LIBRARY: many lambda GT11 cDNA and genomic libraries
                (B) CLONE: synthesis of 14 clones (x) PUBLICATION INFORMATION:
                (A) AUTHORS: Burgoon, M.P.
                        Grumet, M.
                        Mauro, V.
                        Edelman, G.M.
                        Cunningham, B.A.
                (B) TITLE: Structure of the chicken neuron-
                        glial cell adhesion molecule, Ng-CAM:
                        Origin of the polypeptides and
                        relation to the Ig superfamily.
                (C) JOURNAL: J. Cell Biol.
                (D) VOLUME: 112
                (E) ISSUE:
                (F) PAGES: 1017-1029

(G) DATE: 1991

(xi) SEQUENCE DESCRIPTION: SEQ ID NO: 38:

| Phe | Gly | Val | Gly | Gly | Arg | Gly | Gly | Phe | His | Gly | Ala | Ala | Val | Glu | Phe | Gly |
|---|---|---|---|---|---|---|---|---|---|---|---|---|---|---|---|---|
| 1 | | | | 5 | | | | | 10 | | | | | 15 | | |

| Ala | Ala | Gln | Glu | Asp | Asp | Val | Glu | Phe | Glu | Val | Gln | Phe | Met | Asn | Lys | Ser |
|---|---|---|---|---|---|---|---|---|---|---|---|---|---|---|---|---|
| | | | 20 | | | | 25 | | | | | 30 | | | | |

| Thr | Asp | Glu | Pro | Trp | Arg | Thr | Ser | Gly | Arg | Ala | Asn | Ser | Ser | Leu | Arg | Arg |
|---|---|---|---|---|---|---|---|---|---|---|---|---|---|---|---|---|
| 35 | | | | | 40 | | | | | 45 | | | | | 50 | |

| Tyr | Arg | Leu | Glu | Gly | Leu | Arg | Pro | Gly | Thr | Ala | Tyr | Arg | Val | Gln | Phe | Val |
|---|---|---|---|---|---|---|---|---|---|---|---|---|---|---|---|---|
| | | | 55 | | | | | 60 | | | | | 65 | | | |

| Gly | Arg | Asn | Arg | Ser | Gly | Glu | Asn | Val | Ala | Phe | Trp | Glu | Ser | Glu | Val | Gln |
|---|---|---|---|---|---|---|---|---|---|---|---|---|---|---|---|---|
| 70 | | | | | 75 | | | | | 80 | | | | | 85 | |

| Thr | Asn | Gly | Thr | Val | Val | Pro | Gln |
|---|---|---|---|---|---|---|---|
| | | | 90 | | | | |

(2) INFORMATION FOR SEQ ID NO:39:

(i) SEQUENCE CHARACTERISTICS:
        (A) LENGTH: 144
        (B) TYPE: amino acid
        (C) STRANDEDNESS: single
        (D) TOPOLOGY: linear (ii) MOLECULE TYPE: amino acids (iii) HYPOTHETICAL: irrelevant (iv) ANTI-SENSE: no (v) ORIGINAL SOURCE:
        (A) ORGANISM: CHICKEN
        (B) INDIVIDUAL ISOLATE: e9-e14 embryos brains, adult brains (vii) IMMEDIATE SOURCE:
        (A) LIBRARY: many lambda GT11 cDNA and genomic libraries
        (B) CLONE: synthesis of 14 clones (x) PUBLICATION INFORMATION:
        (A) AUTHORS: Burgoon, M.P.
                Grumet, M.
                Mauro, V.
                Edelman, G.M.
                Cunningham, B.A.
        (B) TITLE: Structure of the chicken neuron-
                glial cell adhesion molecule, Ng-CAM:
                Origin of the polypeptides and
                relation to the Ig superfamily.
        (C) JOURNAL: J. Cell Biol.
        (D) VOLUME: 112
        (E) ISSUE:
        (F) PAGES: 1017-1029
        (G) DATE: 1991

(xi) SEQUENCE DESCRIPTION: SEQ ID NO: 39:

| Pro | Gly | Gly | Gly | Val | Cys | Thr | Lys | Gly | Trp | Phe | Ile | Gly | Phe | Val | Ser | Ser |
|---|---|---|---|---|---|---|---|---|---|---|---|---|---|---|---|---|
| 1 | | | | 5 | | | | | 10 | | | | | 15 | | |

| Val | Val | Leu | Leu | Leu | Leu | Ile | Leu | Leu | Ile | Leu | Cys | Phe | Ile | Lys | Arg | Ser |
|---|---|---|---|---|---|---|---|---|---|---|---|---|---|---|---|---|
| | | | 20 | | | | 25 | | | | | 30 | | | | |

| Lys | Gly | Gly | Lys | Tyr | Ser | Val | Lys | Asp | Lys | Glu | Asp | Thr | Gln | Val | Asp | Ser |
|---|---|---|---|---|---|---|---|---|---|---|---|---|---|---|---|---|
| 35 | | | | | 40 | | | | | 45 | | | | | 50 | |

| Glu | Ala | Arg | Pro | Met | Lys | Asp | Glu | Thr | Phe | Gly | Glu | Tyr | Arg | Ser | Leu | Glu |
|---|---|---|---|---|---|---|---|---|---|---|---|---|---|---|---|---|
| | | | 55 | | | | | 60 | | | | | 65 | | | |

| Ser | Glu | Ala | Glu | Lys | Gly | Ser | Ala | Ser | Gly | Ser | Gly | Ala | Gly | Ser | Gly | Val |
|---|---|---|---|---|---|---|---|---|---|---|---|---|---|---|---|---|
| | 70 | | | | | 75 | | | | | 80 | | | | | 85 |

| Gly | Ser | Pro | Gly | Arg | Gly | Pro | Cys | Ala | Ala | Gly | Ser | Glu | Asp | Ser | Leu | Ala |
|---|---|---|---|---|---|---|---|---|---|---|---|---|---|---|---|---|
| | | | | 90 | | | | 95 | | | | | 100 | | | |

-continued

| | | | | | | | | | | | | | | |
|---|---|---|---|---|---|---|---|---|---|---|---|---|---|---|
| Gly | Tyr | Gly 105 | Gly | Ser | Gly | Asp | Val 110 | Gln | Phe | Asn | Glu | Asp 115 | Gly | Ser | Phe | Ile |
| Gly 120 | Gln | Tyr | Arg | Gly | Pro 125 | Gly | Ala | Gly | Pro | Gly 130 | Ser | Ser | Gly | Pro | Ala 135 | Ser |
| Pro | Cys | Ala | Gly 140 | Pro | Pro | Leu | Asp | | | | | | | | |

Having thus described the preferred embodiments, the invention is now claimed to be:

1. The human L1 cell adhesion molecule encoded by the isolated DNA molecule (SEQ ID NO: 1) identified in FIGS. 3A amd 3B.

2. The human L1 cell adhesion molecule of claim 1, wherein said human L1 cell adhesion molecule comprises 1,256 amino acids and is of 142,698 Dalton molecular weight.

3. A cloning vector comprising the isolated DNA molecule (SEQ ID NO: 1) identified in FIGS. 3A and 3B.

* * * * *